US009672726B2

(12) United States Patent
Borke et al.

(10) Patent No.: US 9,672,726 B2
(45) Date of Patent: Jun. 6, 2017

(54) HAND HYGIENE COMPLIANCE MONITORING SYSTEM

(75) Inventors: Brian S. Borke, Appleton, WI (US); Andre Lanouette, Appleton, WI (US)

(73) Assignee: Georgia-Pacific Consumer Products LP, Atlanta, GA (US)

(*) Notice: Subject to any disclaimer, the term of this patent is extended or adjusted under 35 U.S.C. 154(b) by 686 days.

(21) Appl. No.: 13/291,679

(22) Filed: Nov. 8, 2011

(65) Prior Publication Data

US 2012/0112906 A1 May 10, 2012

Related U.S. Application Data

(60) Provisional application No. 61/411,240, filed on Nov. 8, 2010.

(51) Int. Cl.

| G08B 1/08 | (2006.01) |
|---|---|
| G08B 13/14 | (2006.01) |
| G08B 23/00 | (2006.01) |
| G08B 25/00 | (2006.01) |
| G08B 21/24 | (2006.01) |
| G06F 19/00 | (2011.01) |

(52) U.S. Cl.
CPC ......... G08B 21/245 (2013.01); G06F 19/327 (2013.01)

(58) Field of Classification Search
CPC .............. G08B 21/245; G08B 13/2462; G08B 21/0423; G08B 21/0453; G06F 19/327; G06F 19/3418; G06F 19/3431; G06F 19/3443
USPC ........ 340/539.13, 539.12, 573.1, 572.1, 571, 340/307
See application file for complete search history.

(56) References Cited

U.S. PATENT DOCUMENTS

| 3,967,478 A | 7/1976 | Guinn |
|---|---|---|
| 4,606,085 A | 8/1986 | Davies |
| 4,814,751 A | 3/1989 | Hawkins et al. |
| 4,896,144 A | 1/1990 | Bogstad |

(Continued)

FOREIGN PATENT DOCUMENTS

| EP | 0768702 A1 | 2/1997 |
|---|---|---|
| EP | 0921506 A1 | 6/1999 |

(Continued)

OTHER PUBLICATIONS

International Search Report and Written Opinion of the International Searching Authority for PCT/US2011/059747 mailed Jun. 1, 2012.

(Continued)

*Primary Examiner* — Emily C Terrell
(74) *Attorney, Agent, or Firm* — Alston & Bird LLP

(57) ABSTRACT

A hand hygiene compliance monitoring system includes a method and computer program product for performing sanitation compliance monitoring including receiving sanitation compliance data. The sanitation compliance data includes a zone identifier corresponding to a first device in a zone and an entity identifier corresponding to a second device attached to a mobile entity in the zone. The zone is defined by an area over which the first device and the second device communicate via one-way or two-way communication. It is determined whether the entity is compliant with a sanitation protocol associated with the zone, and a database is updated with results of the determining.

20 Claims, 12 Drawing Sheets

(56) References Cited

U.S. PATENT DOCUMENTS

| | | |
|---|---|---|
| 4,990,892 A | 2/1991 | Guest et al. |
| 5,199,118 A | 4/1993 | Cole et al. |
| 5,202,666 A | 4/1993 | Knippscheer |
| 5,204,670 A | 4/1993 | Stinton |
| 5,572,195 A | 11/1996 | Heller et al. |
| 5,610,589 A | 3/1997 | Evans et al. |
| 5,629,678 A | 5/1997 | Gargano et al. |
| 5,661,459 A | 8/1997 | Belcher |
| 5,670,945 A | 9/1997 | Applonie |
| 5,695,091 A | 12/1997 | Winings |
| 5,745,039 A | 4/1998 | Hof et al. |
| 5,771,925 A | 6/1998 | Lewandowski |
| 5,793,653 A | 8/1998 | Segal |
| 5,808,553 A | 9/1998 | Cunningham |
| 5,812,059 A | 9/1998 | Shaw et al. |
| 5,870,015 A | 2/1999 | Hinkel |
| 5,900,067 A | 5/1999 | Jones |
| 5,900,801 A | 5/1999 | Heagle et al. |
| 5,917,425 A | 6/1999 | Crimmins |
| 5,939,974 A | 8/1999 | Heagle et al. |
| 5,945,910 A | 8/1999 | Gorra |
| 5,952,924 A | 9/1999 | Evans et al. |
| 5,954,069 A | 9/1999 | Foster |
| 5,960,991 A | 10/1999 | Ophardt |
| 5,966,753 A | 10/1999 | Gauthier et al. |
| 6,029,600 A | 2/2000 | Davis |
| 6,031,461 A | 2/2000 | Lynn |
| 6,038,331 A | 3/2000 | Johnson |
| 6,104,295 A | 8/2000 | Gaisser et al. |
| 6,125,482 A | 10/2000 | Foster |
| 6,147,607 A | 11/2000 | Lynn |
| 6,154,139 A | 11/2000 | Heller |
| 6,169,484 B1 | 1/2001 | Schuchman et al. |
| 6,206,238 B1 | 3/2001 | Ophardt |
| 6,211,788 B1 | 4/2001 | Lynn et al. |
| 6,236,317 B1 | 5/2001 | Cohen et al. |
| 6,236,953 B1 | 5/2001 | Segal |
| 6,278,372 B1 | 8/2001 | Velasco, Jr. et al. |
| 6,344,794 B1 | 2/2002 | Ulrich et al. |
| 6,375,038 B1 | 4/2002 | Daansen et al. |
| 6,392,546 B1 | 5/2002 | Smith |
| 6,404,837 B1 | 6/2002 | Thompson et al. |
| 6,426,701 B1 | 7/2002 | Levy et al. |
| 6,433,689 B1 | 8/2002 | Hovind et al. |
| 6,462,656 B2 | 10/2002 | Ulrich et al. |
| 6,523,193 B2 | 2/2003 | Saraya |
| 6,536,060 B1 | 3/2003 | Janssens et al. |
| 6,539,393 B1 | 3/2003 | Kabala |
| 6,542,568 B1 | 4/2003 | Howes, Jr. et al. |
| 6,577,240 B2 | 6/2003 | Armstrong |
| 6,707,873 B2 | 3/2004 | Thompson et al. |
| 6,727,818 B1 | 4/2004 | Wildman et al. |
| 6,825,763 B2 | 11/2004 | Ulrich et al. |
| 6,832,916 B2 | 12/2004 | Collopy |
| 6,838,992 B2 | 1/2005 | Tenarvitz |
| 6,882,278 B2 | 4/2005 | Winings et al. |
| 6,883,563 B2 | 4/2005 | Smith |
| 6,933,849 B2 | 8/2005 | Swayer |
| 6,954,148 B2 | 10/2005 | Pulkkinen et al. |
| 6,970,574 B1 | 11/2005 | Johnson |
| 6,972,677 B2 * | 12/2005 | Coulthard .................... 340/531 |
| 6,975,231 B2 | 12/2005 | Lane et al. |
| 6,992,561 B2 | 1/2006 | Sandt et al. |
| 7,015,816 B2 | 3/2006 | Wildman et al. |
| 7,019,644 B2 | 3/2006 | Barrie |
| 7,080,061 B2 | 7/2006 | Kabala |
| 7,099,895 B2 | 8/2006 | Dempsey |
| 7,150,284 B2 | 12/2006 | Aulbers et al. |
| 7,163,101 B2 | 1/2007 | Harper |
| 7,242,307 B1 | 7/2007 | LeBlond et al. |
| 7,271,728 B2 | 9/2007 | Taylor et al. |
| 7,285,114 B2 | 10/2007 | Harper |
| 7,286,057 B2 | 10/2007 | Bolling |
| 7,293,645 B2 | 11/2007 | Harper et al. |
| 7,311,523 B2 | 12/2007 | Collopy |
| 7,315,245 B2 | 1/2008 | Lynn et al. |
| 7,322,370 B2 | 1/2008 | Aulbers et al. |
| 7,372,367 B2 | 5/2008 | Lane et al. |
| 7,375,640 B1 | 5/2008 | Plost |
| 7,408,470 B2 | 8/2008 | Wildman et al. |
| 7,411,511 B2 | 8/2008 | Kennish et al. |
| 7,423,533 B1 | 9/2008 | LeBlond et al. |
| 7,425,900 B2 | 9/2008 | Lynn et al. |
| 7,443,302 B2 | 10/2008 | Reeder et al. |
| 7,443,304 B2 | 10/2008 | Rowe et al. |
| 7,443,305 B2 | 10/2008 | Verdiramo |
| 7,451,894 B2 | 11/2008 | Ophardt |
| 7,477,148 B2 | 1/2009 | Lynn et al. |
| 7,482,936 B2 | 1/2009 | Bolling |
| 7,495,569 B2 | 2/2009 | Pittz |
| 7,542,586 B2 | 6/2009 | Johnson |
| 7,551,089 B2 | 6/2009 | Sawyer |
| 7,551,092 B1 | 6/2009 | Henry |
| 7,597,122 B1 | 10/2009 | Smith |
| 7,605,704 B2 | 10/2009 | Munro et al. |
| 7,616,122 B2 | 11/2009 | Bolling |
| 7,659,824 B2 | 2/2010 | Prodanovich et al. |
| 7,676,380 B2 | 3/2010 | Graves et al. |
| 7,682,464 B2 | 3/2010 | Glenn et al. |
| 7,698,770 B2 | 4/2010 | Barnhill et al. |
| 7,755,494 B2 | 7/2010 | Melker et al. |
| 7,770,782 B2 | 8/2010 | Sahud |
| 7,804,409 B2 | 9/2010 | Munro et al. |
| 7,812,730 B2 | 10/2010 | Wildman et al. |
| 7,818,083 B2 | 10/2010 | Glenn et al. |
| 7,825,812 B2 | 11/2010 | Ogrin et al. |
| 7,855,651 B2 | 12/2010 | LeBlond et al. |
| 7,898,407 B2 | 3/2011 | Hufton et al. |
| 8,040,245 B2 * | 10/2011 | Koblasz .................... 340/573.1 |
| 8,164,439 B2 * | 4/2012 | Dempsey et al. ........ 340/539.12 |
| 2002/0082177 A1 | 6/2002 | Tabaac |
| 2002/0135486 A1 | 9/2002 | Brohagen et al. |
| 2002/0175182 A1 | 11/2002 | Matthews |
| 2003/0164456 A1 | 9/2003 | Petrich et al. |
| 2003/0197122 A1 | 10/2003 | Faiola et al. |
| 2004/0138535 A1 * | 7/2004 | Ogilvie .......................... 600/300 |
| 2004/0150527 A1 | 8/2004 | Harper et al. |
| 2005/0134465 A1 | 6/2005 | Rice et al. |
| 2005/0171634 A1 | 8/2005 | York et al. |
| 2006/0272361 A1 | 12/2006 | Snodgrass |
| 2006/0273915 A1 | 12/2006 | Snodgrass |
| 2006/0277065 A1 | 12/2006 | Guten et al. |
| 2006/0282459 A1 | 12/2006 | Kabala |
| 2007/0015552 A1 | 1/2007 | Bolling |
| 2007/0020212 A1 | 1/2007 | Bernal et al. |
| 2007/0096930 A1 | 5/2007 | Cardoso |
| 2007/0229288 A1 | 10/2007 | Ogrin et al. |
| 2007/0288263 A1 | 12/2007 | Rodgers |
| 2008/0001763 A1 | 1/2008 | Raja et al. |
| 2008/0019489 A1 | 1/2008 | Lynn |
| 2008/0019490 A1 | 1/2008 | Lynn |
| 2008/0021779 A1 | 1/2008 | Lynn et al. |
| 2008/0031838 A1 | 2/2008 | Bolling |
| 2008/0087309 A1 | 4/2008 | Aulbers et al. |
| 2008/0087719 A1 | 4/2008 | Sahud |
| 2008/0106374 A1 | 5/2008 | Sharbaugh |
| 2008/0131332 A1 | 6/2008 | Nguyen et al. |
| 2008/0136649 A1 | 6/2008 | Van De Hey |
| 2008/0185395 A1 | 8/2008 | Sahud |
| 2008/0246599 A1 | 10/2008 | Hufton et al. |
| 2008/0266113 A1 | 10/2008 | Kennish |
| 2008/0290112 A1 | 11/2008 | Lynn |
| 2009/0010106 A1 | 1/2009 | Levy |
| 2009/0068116 A1 | 3/2009 | Arndt |
| 2009/0084407 A1 | 4/2009 | Glenn et al. |
| 2009/0091458 A1 | 4/2009 | Deutsch |
| 2009/0112630 A1 | 4/2009 | Collins, Jr. |
| 2009/0119142 A1 | 5/2009 | Yenni et al. |
| 2009/0189759 A1 | 7/2009 | Wildman et al. |
| 2009/0195385 A1 | 8/2009 | Huang et al. |
| 2009/0202425 A1 | 8/2009 | Park et al. |
| 2009/0204256 A1 | 8/2009 | Wegelin |
| 2009/0219131 A1 | 9/2009 | Barnett et al. |
| 2009/0224907 A1 | 9/2009 | Sinha et al. |

(56) References Cited

U.S. PATENT DOCUMENTS

| | | |
|---|---|---|
| 2009/0224924 A1 | 9/2009 | Thorp |
| 2009/0237254 A1 | 9/2009 | Munro et al. |
| 2009/0237651 A1 | 9/2009 | Arndt et al. |
| 2009/0265990 A1 | 10/2009 | Stratmann |
| 2009/0267776 A1 | 10/2009 | Glenn et al. |
| 2009/0272405 A1 | 11/2009 | Barnhill et al. |
| 2009/0273477 A1 | 11/2009 | Barnhill |
| 2009/0276239 A1 | 11/2009 | Swart et al. |
| 2009/0295539 A1 | 12/2009 | Mahmoodi et al. |
| 2009/0295582 A1 | 12/2009 | Sawyer |
| 2009/0299787 A1 | 12/2009 | Barnhill |
| 2009/0301523 A1 | 12/2009 | Barnhill et al. |
| 2009/0324444 A1 | 12/2009 | Stratmann |
| 2010/0069087 A1 | 3/2010 | Chow et al. |
| 2010/0073162 A1 | 3/2010 | Johnson et al. |
| 2010/0094581 A1 | 4/2010 | Cagle |
| 2010/0097224 A1 | 4/2010 | Prodanovich et al. |
| 2010/0109877 A1 | 5/2010 | Bolling |
| 2010/0117823 A1 | 5/2010 | Wholtjen |
| 2010/0117836 A1 | 5/2010 | Momen et al. |
| 2010/0123560 A1 | 5/2010 | Nix et al. |
| 2010/0134296 A1 | 6/2010 | Hwang |
| 2010/0155416 A1 | 6/2010 | Johnson |
| 2010/0188228 A1 | 7/2010 | Hyland |
| 2010/0230435 A1 | 9/2010 | Wegelin |
| 2010/0238021 A1 | 9/2010 | Harris |
| 2010/0265059 A1 | 10/2010 | Melker et al. |
| 2010/0315244 A1 | 12/2010 | Tokhtuev |
| 2010/0321187 A1 | 12/2010 | Raccio |
| 2010/0328076 A1 | 12/2010 | Kyle et al. |
| 2010/0332022 A1 | 12/2010 | Wegelin et al. |
| 2011/0025509 A1 | 2/2011 | Brow |
| 2011/0273298 A1 | 11/2011 | Snodgrass et al. |
| 2011/0291840 A1 | 12/2011 | Pelland et al. |
| 2012/0112906 A1 | 5/2012 | Borke et al. |
| 2014/0135588 A1* | 5/2014 | Al-Ali et al. .......... 600/300 |

FOREIGN PATENT DOCUMENTS

| | | |
|---|---|---|
| EP | 1913892 A2 | 4/2008 |
| GB | 2298851 A1 | 9/1996 |
| GB | 2324397 A | 10/1998 |
| GB | 2425388 A | 10/2006 |
| JP | 62132161 A | 6/1987 |
| JP | 1219439 A | 9/1989 |
| JP | 9159768 A | 6/1997 |
| JP | 11332961 A | 12/1999 |
| JP | 2001292918 A | 1/2001 |
| WO | 00/68908 A1 | 11/2000 |
| WO | 02/077927 A1 | 10/2002 |
| WO | 2006-135922 A2 | 12/2006 |
| WO | 2008/119158 A1 | 10/2008 |
| WO | 2010/026581 A1 | 3/2010 |
| WO | 2010/034125 A1 | 4/2010 |
| WO | 2010/099488 A1 | 9/2010 |
| WO | 2010/101929 A2 | 9/2010 |
| WO | 2010/141689 A2 | 9/2010 |

OTHER PUBLICATIONS

International Search Report and Written Opinion of the International Searching Authority for PCT/US2011/037667 mailed Jan. 5, 2012.
"Clean Hands—How it Works", http://www.cleanhands.biz/how.htm, printed Apr. 29, 2013, 2 pages, Clean Hands.
"VER-8610 Reports Plus", 2009, 2 pages, Versus Technologies, Inc.
VISion Enterprise Locating Solutions—"Hand Hygiene Compliance", 2009, 2 pages, Versus Technologies, Inc.
VISion Enterprise Locating Solutions—"Clinic Success Story", 2009, 1 page, Versus Technologies, Inc.
VISion Enterprise Locating Solutions—"Nurse Call", 2008, 1 page, Versus Technologies, Inc.
"VER-1780 Personnel Alert Badge (IR/RF)", 2008, 1 page, Versus Technologies, Inc.
"VER-1920 Flex Badge (IR/RF)", 2009, 1 page, Versus Technologies, Inc.
"VER-8235 History List View", 2008, 1 page, Versus Technologies, Inc.
"VER-8250 Rules Engine", 2008, 1 page, Versus Technologies, Inc.
"VISion Enterprise Locating Solutions", Brochure, 2008, 8 pages, Versus Technologies, Inc.
"AeroScout—AeroScout MobileView", 2011, 2 pages, 2011, Aeroscout, Inc.
"AeroScout—Hand Hygiene Compliance Monitoring—Application Note", 2 pages, 2011, AeroScout, Inc.
"Real-Time Location Systems (RTLS)", Feb. 2011, 2 pages, Centrak, Inc.
"A Secure Exit—Keep Wandering Patients Safe & Secure", 2010, 2 pages, Visonic Technologies, Ltd.
"Safety, Security & Visibility", Brochure, 2011, 4 pages, Visonic Technologies, Ltd.
"Amelior 360—Hand Hygiene—The Unique Real-Time Hand Hygiene Compliance Module", Brochure, 2011, 4 pages, Patient Care Technology Systems.
"Heathcare—Equipment Manufacturers", 2011, 1 page, AiRISTA, LLC.
"Monitrac TS Temperature Monitoring", 2010, 2 pages, AiRISTA, LLC.
"Solutions for Healthcare", 2010, 2 pages, AiRISTA, LLC.
"Monitrac Senior Living Solution", 2010, 2 pages, AiRISTA, LLC.
"Hill-Rom's Handwashing Compliance Solution", Apr. 22, 2010, 2 pages, Hill-Rom Services, Inc.
"Proventix Partners with Synapse Wireless to Save Lives", http://www.prnewswire.com/news-releases/proventix-partners-with-synapse-wireless-to-sa . . . , printed Jul. 16, 2010, 4 pages, PR Newswire.
"Using Zigbee to Monitor Hand Hygiene Compliance", http://www.themobilehealthcrowd.com/?q=node/207, printed May 11, 2010, 2 pages, theMobileHealthCrowd.
"Whitepaper—Methodologies for Sharply Reducing Hospital-Acquired Infections", 7 pages, Dynamic Computer Corporation, Date Unknown.
Zieger, Anne; "Case Study: FL Hospital Uses IT to Monitor Hand Washing", http://www.fiercehealthit.com/node/8503/, Aug. 3, 2009, 1 page, Fierce Health It.
"Hand Washing Compliance Monitoring", http://www.centrak.com/solutions_hhc_monitoring.aspx, Printed Nov. 1, 2010, 1 page, Centrak Inc.
"CenTrak Acquires Important Patent for Dual Infrared/Radio Frequency (IR/RF Technology; IR/RF Approach Enables 100% Room-Level Location Accuracy: U.S. Pat. No. 5,917,425 'Infrared and RF Location System'", Press Release, http://www.centrak.com/PressRelease_08_06_2008. aspx, Jul. 8, 2008, Centrak Inc.
"Automated Hand Hygiene Compliance", http://www.pcts.com/unified/handhygiene.php, 2009, 2 pages, Patient Care Technology Systems.
"Hand Wash Monitoring System Provides Full Accountability", http://www.handgienecorp.com/pdf/handGiene_Healthcare.pdf, 4 pages, Date Unknown, HandGiene Corp.
"Henry Tenarvitz of Versus Technology Speaks About RTLS at 'Meaningful Use Beyond EMRs' Event", http://www.dynamicrfidsolutions.com/blog/?p=623, Oct. 15, 2009, 4 pages, Dynamic Computer Corporation.
"Net/Tech to Unveil Patented Hygiene Guard Hand-Washing Monitoring System at the National Restaurant Show", http://findarticles.com/p/articles/mi_m0EIN/is_1997_April 3/ai_19277592/, Apr. 3, 1997, 2 pages, Business Wire.
"Net/Tech International, Inc. to Participate in Discovery Expo '97 at New York Hilton Jul. 9", http://www.prnewswire.com/news-releases/nettech-international-inc-to-participate-in-disc . . . , Jul. 7, 1997, 1 pages, PR Newswire.
"Michigan IT Companies Helping the University of Miami Center for Patient Safety Tackle a Leading Cause of Death Using an RTLS

(56) References Cited

OTHER PUBLICATIONS

Solution to Monitor Staff Hand-Washing Compliance", Jul. 29, 2009, 2 pages, VERSUS Accuracy Matters and Dynamic Computer Corporation.

Ali, Farida, "Will RFID Improve Hygiene in Hospitals?", Jun. 24, 2010, 3 pages, Dynamic Computer Corporation.

"How It Works", http://handgienecorp.com/howItWorks.php, printed Sep. 28, 2010, 1 page, HandGiene Corp.

"nGage", http://www.proventix.com/Products.aspx, printed Sep. 28, 2010, 2 pages, Proventix.

United States Patent and Trademark Office, Office Action for U.S. Appl. No. 13/114,216, Jun. 28, 2013, 40 pages, USA.

J.M. Broughall, et al, "An Automatic Monitoring Systems for Measuring Handwashing Frequency in Hospital Wards", Journal of Hospital Infection, 1984, pp. 447-453, vol. 5, The Hospital Infection Society, 1984.

Denise M. Korniewicz, et al. "Exploting the Factors Associated with Hand Hygiene Compliance of Nurses During Routine Clinical Practice", Applied Nursing Research, 2010, pp. 86-90, vol. 23, Elsevier.

Andrew G. Sahud, et al, "An Electronic Hand Hygiene Surveillance Device: A Pilot Study Exploring Surrogate Markers for Hand Hygiene Compliance", Infection Control and Hospital Epidemiology, Jun. 2010, pp. 634-639, vol. 31, No. 6, The Society for Healthcare Epidemiology of America.

Philip M. Polgreen, et al, "Method for Automated Monitoring of Hand Hygiene Adherence Without Radio-Frequency Identification", Infection Control and Hospital Epidemiology, Dec. 2010, pp. 1294-1295, vol. No. 12, The Society for Healthcare Epidemiology of America.

\* cited by examiner

HAND HYGIENE COMPLIANCE MONITORING SYSTEM

CROSS REFERENCE TO RELATED APPLICATIONS

The present application claims the benefit of U.S. Provisional Application No. 61/411,240 filed Nov. 8, 2010, the content of which is hereby incorporated by reference in its entirety.

BACKGROUND OF THE INVENTION

The subject matter disclosed herein relates generally to hand hygiene compliance and particularly to tracking and encouraging worker compliance with hand hygiene protocols.

In a hospital setting, hospital associated infections may cause undue illness to patients. One way of decreasing the number of hospital associated infections is for hospital workers to wash their hands at key phases of patient care. In an effort to reduce the number of hospital associated infections, hospitals have implemented hand hygiene protocols for hospital staff. For example, staff at a hospital may be instructed to wash their hands when they enter a patient room, before any patient contact, before an aseptic task, after body fluid exposure risk, after patient contact, after contact with patient surroundings, and upon exiting the patient room.

Hospitals have a variety of techniques for reminding workers to follow hand hygiene protocols and for tracking worker compliance with hand hygiene protocols. One method of reminding workers to follow hand hygiene protocols is to send a signal (e.g., an audio or visual reminder) to the health care worker (HCW) when the health care worker enters or exits a patient's room. This method works well when hand hygiene requirements are the same for all patients and when the requirements are associated with a health care worker being at a particular location. One method of tracking hand hygiene compliance is to use "secret shoppers" to watch the staff to see if they are following the protocol. The secret shoppers may remind the health care workers and/or they may report on compliance. One drawback to the use of secret shoppers is that knowledge of the presence of the secret shoppers on particular days can cause an artificial spike in hand hygiene compliance, because the workers know that they are being watched.

Accordingly, there remains a need in the art for hand hygiene compliance systems that overcome these drawbacks.

This background information is provided to reveal information believed by the applicant to be of possible relevance to the present invention. No admission is necessarily intended, nor should be construed, that any of the preceding information constitutes prior art against the present invention.

BRIEF DESCRIPTION OF THE INVENTION

Embodiments include a method and computer program product for performing sanitation compliance monitoring, including receiving sanitation compliance data. The sanitation compliance data includes a zone identifier corresponding to a first device in a zone and an entity identifier corresponding to a second device attached to a mobile entity in the zone. The zone is defined by an area over which the first device and the second device communicate via one-way or two-way communication. It is determined whether the entity is compliant with a sanitation protocol associated with the zone, and a database is updated with results of the determining.

Another embodiment includes a system for performing sanitation compliance monitoring. The system includes a sanitation station configured to accomplish a sanitation event that meets at least one criterion, a mechanism to detect the sanitation event at the sanitation station, a user interface, and a device that includes logic. The logic is for detecting at least one entity identification (ID) tag in proximity of the sanitation station, each entity ID tag including a unique tag identifier corresponding to an entity. The logic is also for selecting an entity ID tag from the at least one detected entity ID tags and for displaying a unique tag identifier associated with the selected entity ID tag, the displaying at the user interface. The logic is further for determining whether the at least one criterion has been met at the sanitation station and for updating a database with results of the determining and the tag identifier associated with the selected entity ID tag.

Other embodiments include a method and computer program product for performing sanitation compliance monitoring including receiving a notification at a circuit in a mobile entity ID tag that a zone ID tag has been detected. Each zone ID tag corresponds to a zone and has a unique zone identifier corresponding to the zone ID tag. The mobile entity ID tag is stored in a database on the mobile entity ID tag in response to the receiving. Contents of the database are periodically transmitted to a central computer.

A further embodiment includes a system for performing sanitation compliance monitoring. The system includes a synchronization station that includes a memory; a mechanism to detect a mobile entity ID tag; and logic for receiving data from the mobile entity ID tag, for storing the received data in the memory, and for periodically transmitting contents of the memory to a central computer.

A further embodiment is a system for performing sanitation compliance monitoring. The system includes a first device in communication with a database and a second device in communication with the database. The system also includes a target zone defined by a first area over which a mobile device worn by a health care worker and the first device communicate, and a sanitation zone defined by a second area over which the mobile device worn by the health care worker and the second device communicate. The target zone and the sanitation zone do not overlap.

BRIEF DESCRIPTION OF THE DRAWINGS

Referring to the exemplary drawings wherein like elements are numbered alike in the accompanying Figures:

FIG. 6, which includes

FIG. 8, which includes

FIG. 10, which includes

DETAILED DESCRIPTION OF THE INVENTION

Figure 1:
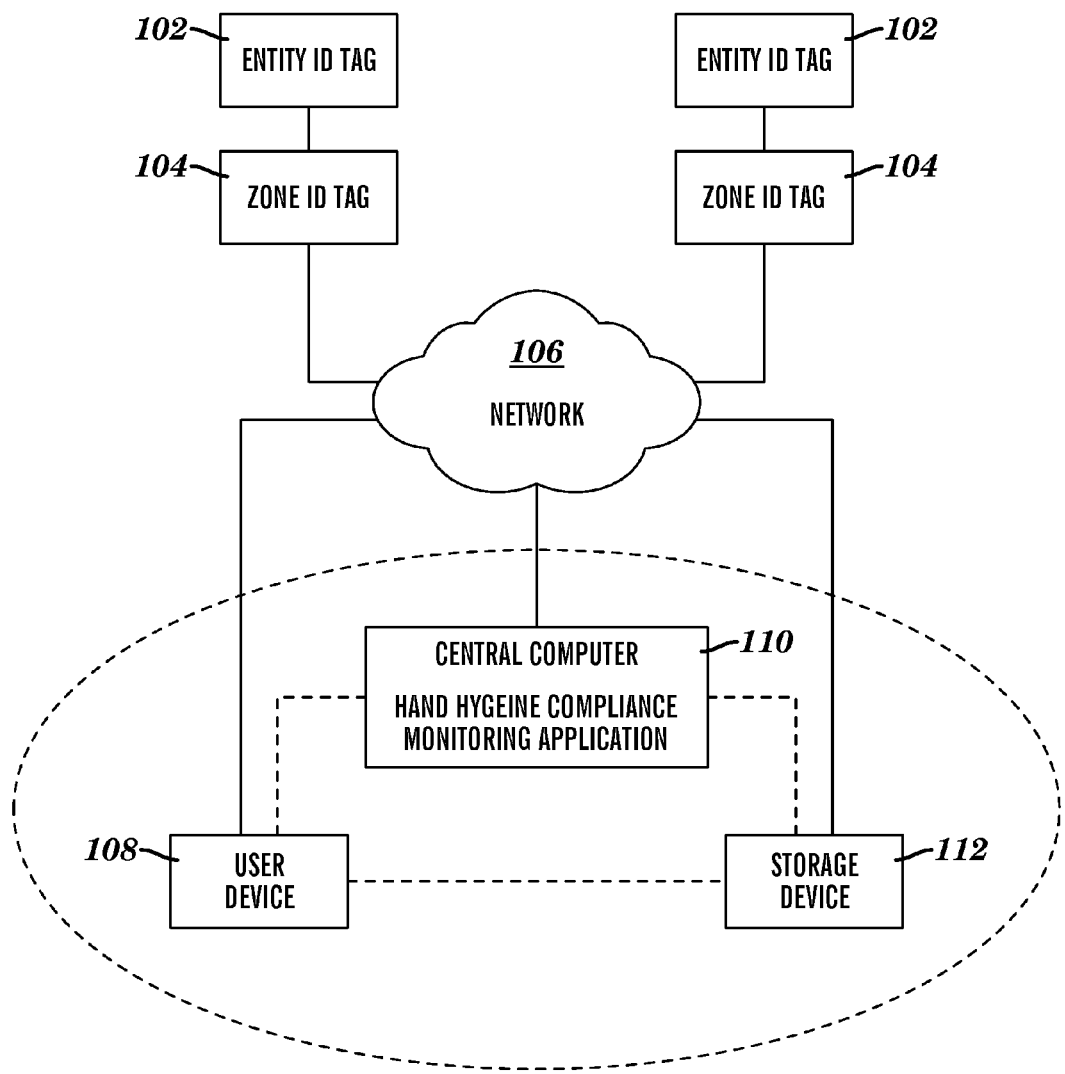
FIG. 1 depicts a hand hygiene compliance system implemented in accordance with an embodiment.

Although the following detailed description contains many specifics for the purposes of illustration, one of ordinary skill in the art will appreciate that many variations and alterations to the following details are within the scope of the invention. Accordingly, the following embodiments of the invention are set forth without any loss of generality to, and without imposing limitations upon, the claimed invention.

Exemplary embodiments of the invention, as shown and described by the various figures and accompanying text, provide a sanitation compliance monitoring system. An embodiment of the system is a zone-based hand hygiene compliance system that monitors healthcare worker compliance with a hand hygiene protocol. Health care workers wear badges that contain radio signal emitting tags for communicating with radio signal reader devices that are located at points of hygiene protocol interest in a facility (e.g., on a hand sanitizer dispenser, on a patient bed). When a health care worker is within a predefined distance of a reader device, the reader device detects the presence of the worker and records data related to the worker. The area around the reader device where the reader device can detect the radio signals begin emitted from a health care worker badge is referred to as a zone. The location of a zone may be stationary or it may be adjustable, for example, by mounting a reader device on a movable arm and repositioning the movable arm. Data related to health care worker hand hygiene protocol compliance and non-compliance is collected by the reader device and stored in a database for generating reports to the health care worker, to a supervisor, and/or to other hand hygiene compliance personnel.

Embodiments also include distributed systems where, for example, badges worn by health care workers or other monitored individuals also include reader devices that collect and store compliance and non-compliance related data. In distributed embodiments, the data stored on a badge is uploaded from the health care worker badge to the database when the health care worker is in a predefined vicinity of a synchronizing station. In addition, an item such as a hand wash station that includes a display may indicate information on the display that may be helpful for the user of the hand wash station, such as identifying the health care worker that is getting credit for the hand wash and whether the health care worker is compliant or non-compliant with a hand wash protocol.

Described herein in accordance with exemplary embodiments is a zone-based radio frequency identification (RFID) system that provides the ability to determine if employees (e.g., health care workers) are compliant with hygiene protocols without requiring an expensive and invasive real time locating system (RTLS) for continuously tracking employees throughout a facility. A RTLS uses wireless technology to continuously track the geographical location of entities (e.g., assets and personnel) in real time by attaching tags that emit signals, such as radio signals, to the tracked entities. The signals emitted by the tags are read automatically and continuously by reader devices in the RTLS, and algorithms are executed by the RTLS to determine current positions of the entities based on the signals that were read by the reader devices. An RTLS uses trilateration and/or triangulation algorithms to determine current positions of entities. Both trilateration and triangulation require additional hardware and/or software infrastructure when compared to the zone-based embodiments described herein.

A RTLS is contrasted with a zone-based system utilized by embodiments described herein. Similar to the RTLS, a zone-based RFID system uses signal emitting tags that are attached to entities (e.g., health care workers, patients) that require tracking. However, the zone-based RFID system described herein does not continuously monitor a current location of an entity. Instead, the zone-based RFID system includes reader devices that are designed to detect signals from entities when the entities are within a specified distance of the reader device. In this manner, zones are formed and when an entity enters and exits a particular zone is determined based on, for example, whether or not the reader device detects a signal from the entity. Thus, the zone-based RFID system tracks whether an entity is within a particular zone and does not require the additional overhead required by the RTLS to determine an actual location of the entity. Further, because the zone-based RFID system only tracks an entity when it is within particular zones in a facility, the RFID system incurs lower operational overhead (e.g., radio band usage, power) and requires less powerful and thus, less costly readers and tags when compared to an RTLS that is required to track an entity at all locations in a facility. In addition, the zone-based RFID system described may also be perceived as being less invasive to the privacy of employees than a RTLS because the zone-based RFID system only tracks an employee when the employee is in an area of interest.

Embodiments described herein are utilized to determine whether staff or other individuals in a facility, such as a medical facility, have washed or sanitized their hands according to policy (or protocol). Embodiments may also be applied to other applications and industries where it is necessary to determine if people or equipment are cleaned or sanitized after and/or before activities that might expose the people/equipment to contamination. Embodiments are described herein in reference to a hospital setting and to hand hygiene compliance. It will be appreciated that embodiments of the invention are not so limited and that embodiments of the invention apply to any location (e.g., manufacturing locations, nursing homes, restaurants) where it is desired to track worker compliance with a specified protocol. Embodiments may be used to determine whether an entity is compliant with any type of sanitation protocol including the hand washing protocol described herein. Thus, sanitation zones are not limited to the hand washing zones described herein, but may also apply other types of sanitation procedures such as those used on feet, or upon entry and exit of clean rooms or other sterile environments. As described herein, different criteria can be applied to different zones As used herein, the term "radio frequency beacon" refers to a device that transmits radio frequency signals. Examples include, but are not limited to, radio towers, and cordless microphones.

As used herein, the term "radio frequency receiver" refers to a device that receives radio frequency signals. Examples include, but are not limited to, radios and televisions.

As used herein, the term "passive radio frequency identification device" or "passive (RFID) device" refers to a device that absorbs one or more radio signals that meet certain criteria, changes the radio signals to add useful information, and uses the absorbed energy to re-transmit the radio signals with the added information. Passive RFID devices are often embedded, for example, on employee badges that are used by employees as entry badges to gain access through various points-of-entry.

As used herein, the term "active RFID device" refers to a device that, if it receives one or more radio signals that meet certain criteria, may transmit one or more different radio signals using its own energy source.

As used herein, the term "synchronizing station" refers to a device (e.g., a wired device and/or a wireless device such as a radio frequency transceiver) that collects information from radio frequency transceivers and relays that information to a processor that is executing all or a portion of the hand hygiene compliance monitoring algorithm. The synchronizing station may be wirelessly connected to the radio frequency transceivers and physically connected to the processor (e.g., via cables and/or fiber optics), although other configurations are possible.

As used herein, the term "RFID reader" refers to a device that 1) transmits a radio signal that causes nearby passive or active RFID badges to transmit different radio signals, 2) is able to perceive and process the different radio signals, and 3) is able to communicate with a synchronizing station or other data collection device. An example of a RFID reader is a building access RFID badge reader.

As used herein, the term "radio frequency transceiver" refers to a device that transmits and receives radio frequency signals and may also perform additional functions that could include processing data and storing data. Examples of radio frequency transceivers include, but are not limited to, RFID readers, active RFID badges, passive RFID badges, Bluetooth® devices, wireless fidelity (WiFi) devices, and wireless synchronizing stations.

As used herein, the term "identification tag" or "ID tag" refers to a radio frequency beacon or radio frequency transceiver. An ID tag transmits a unique tag identifier, such as a number, that is associated with a specific location (e.g., a zone) or mobile entity (e.g., person or mobile equipment).

As used herein, the term "sensor suite" refers to a device that collects input wirelessly, hardwired, or by other connection from at least one source, determines whether one or more required steps have been completed, and provides a corresponding output. A sensor suite may contain a radio frequency transceiver, a radio frequency beacon, a radio frequency receiver, and/or an ID tag.

As used herein, the term "zone" refers to the location area over which a zone ID tag assigned to that zone may be in one-way or two-way communication with at least one different radio frequency transceiver or radio frequency beacon. In an embodiment, zones do not overlap. In accordance with an embodiment, a zone is identified by a passive or active RFID tag that transmits a unique zone identifier in response to queries made by an RFID reader or other radio frequency transceiver.

As used herein, the term "target zone" refers to a zone that may generally contain non-hygienic contamination (waste station, patient bed, etc.) or that may generally be hygienic and intended to avoid contamination (e.g., designated aseptic areas). Generally, zones are identified as areas where a hygiene activity should occur either before entering the zone or upon exiting the zone. Zone ID tags referred to herein as "target zone ID tags" are located on or near the items that contain non-hygienic contamination or should be avoided to avoid contamination, defining target zones.

As used herein, the term "hand wash zone" refers to a zone that contains a sanitation item (a sink, a dispenser, etc.) to wash or otherwise sanitize hands or other contaminated objects. A hand wash zone is an example of a sanitation zone. Zone ID tags referred to herein as "hand wash zone ID tags" are affixed to or in close proximity to the sanitation item, defining the hand wash zones.

As used herein, the term "hand wash" refers to decontaminating the hands of a health care worker by washing with soap and water, by rubbing with hand-sanitizer, or by using some other manner of decontamination. In an embodiment, each target zone is assigned at least one approved hand wash zone. An approved hand wash zone is typically closer in proximity to the target zone than an unapproved hand wash zone, which might be farther away from the target zone, creating a risk that a health care worker may spread contamination through the facility.

In an embodiment, a target zone may be active or inactive. An active target zone is associated with a location that has an aseptic purpose (e.g., an operating room or other area that must remain sterile) or with a location that contains at least one source of contamination (e.g., a waste station), such that it is desired to determine hand-hygiene compliance pertaining to that target zone. An inactive target zone is a target zone that does not need to remain sterile because it is not currently being used for an aseptic purpose, or a target zone that does not have a level of contamination that warrants a determination of hand-hygiene compliance. Some embodiments described herein do not penalize a health care worker for entering an active, non-patient target zone (e.g., a zone that includes a waste station) if the health care worker has not washed his hands since being in the previous target zone. This is based on the assumption that in typical use, a health care worker will be transporting contamination from a patient to the waste station, and it is impractical for the health care worker to wash his hands. In addition, having the health care worker wash his hands in this case will likely be ineffective, since the health care worker will already be transporting contamination between the two target zones.

An embodiment utilizes RFID technology to identify when an entity such as a health care worker or a patient is in a target zone or in a hand wash zone. In an embodiment, entity ID tags include passive RFID devices. One type of an entity ID tag is a health care worker ID tag and another type is a patient ID tag.

The use of a zone-based approach and RFID technology provides several benefits in that this approach does not require a line of sight, it is time-tested and well-understood, there are many readily-available and inexpensive products for purchase, and some ID tags may not require batteries. This is contrasted with a RTLS in which a larger number of more powerful RFID devices are required to provide continuous real-time tracking of the geographical location of all entities being tracked.

In an embodiment, a target zone ID tag includes a RFID reader device that "chirps" a specific radio frequency that induces passive and/or active ID tags (e.g., health care worker ID tags and patient ID tags) to transmit their unique tag identifiers if they are in close enough proximity to communicate with the RFID reader. In an embodiment, for each entity ID tag (e.g., health care worker ID tag, patient ID tag) that the target zone ID tag identifies, the target zone ID tag sends its own unique tag identifier along with the unique identifier associated with the identified entity ID tag and an optional timestamp to a data collection device. In an embodiment, the target zone ID tag is able to identify multiple passive and/or active RFID tags at a time.

In an embodiment, a target zone ID tag may be assigned to a zone for ongoing contamination (e.g., waste station), and the hand hygiene compliance system may always consider the zone to be "active." If a target zone ID tag is assigned to a zone that may be temporarily uncontaminated (e.g., an unoccupied patient bed), the hand hygiene compliance system may only consider the zone "active" if the target zone ID tag detects a patient ID tag in the target zone. In this embodiment, the presence of a patient may be detected via the use of a patient ID tag that the patient is wearing (e.g., a wrist bracelet) or that is located proximate to a patient (e.g., close to the location of the patient, such attached to the patient's bed).

The effective distance of a zone is dependent upon the specific hardware used for each ID tag in the system. In an embodiment, customers may require that different zones have different sensing ranges. For example, there are commercially available RFID readers that have ranges from a few millimeters to several meters. Thus, RFID readers with different ranges may be used by an implementation of the hand hygiene compliance system to provide zones of varying sizes based on the needs of the customer.

FIG. 1 depicts a hand hygiene compliance system implemented in accordance with an embodiment. The system depicted in FIG. 1 includes a plurality of entity ID tags 102 (e.g., health care worker ID tags and patient ID tags) that can communicate with zone ID tags 104 (e.g., target zone ID tags and hand wash zone ID tags). The zone ID tags 104 shown in FIG. 1 are in communication with a central computer 110 via a network 106 for transmitting data to a hand hygiene compliance monitoring application executing on the central computer 110. In an embodiment, the network 106 is implemented by a local area network (LAN). It will be appreciated that network 106 can be implemented using other types of wired and wireless networks such as, but not limited to the Internet and an intranet. As depicted in FIG. 1, the network 106 is in communication with the zone ID tags 104, the central computer 110, a storage device 112, and a user device 108. In an embodiment, the central computer 110, the storage device 112, and the user device 108 are located in the same geographical location. In another embodiment, the central computer 110, the storage device 112, and the user device 108 are located in two or more different geographical locations.

The user device 108 depicted in FIG. 1 is utilized to access the hand hygiene compliance monitoring application executing on the central computer 110. In an embodiment, the hand hygiene compliance monitoring application includes software instructions to receive data from the zone ID tags 104 and to perform functions described herein related to monitoring hand hygiene compliance. Embodiments of the hand hygiene compliance monitoring application provide summary reports related to hand hygiene compliance. In an embodiment, the user device 108 is used to monitor hand hygiene compliance data (current and/or past data) related to all or a selected portion of a facility (e.g., a room, a floor, a department). In an embodiment, access to the hand hygiene compliance data is restricted and only authorized users are provided access to all or selected portions of the hand hygiene compliance data. For example, in a hospital setting, one user may be able to access hand hygiene compliance data for only one room, while another user may be able to access hand hygiene compliance data for a group of rooms or for an entire floor. In addition, a user may only be able to access his own hand hygiene compliance data, while another user who supervises a group of employees may be able to access hand hygiene compliance data for any employee in the group. In an embodiment, current hand hygiene compliance data is stored in storage device 112 and status is monitored via the user device 108.

Zone ID tags, such as zone ID tag 104, may be mounted in a variety of manners. In one embodiment, a zone ID tag is mounted on a wall or ceiling or other stationary structure. Alternatively, a zone ID tag may be mounted on a movable arm for desired positioning within arm limits. Zone ID tags may also be mounted on objects such as, but not limited to, a waste basket, an operating room table, and a hand sanitizer dispenser. Any combination of all or a subset of these manners of mounting the zone ID tags may be utilized at an installation of the hand hygiene compliance system. Entity ID tags 102 include health care worker ID tags and patient ID tags. Health care worker ID tags and patient ID tags are typically worn by health care workers and patients in a manner such as, but not limited to, a wrist band, a pocket in a lab coat or shirt, a clip on a belt, and a clip on a necklace.

In an embodiment, at least one of the zone ID tags 104 shown in FIG. 1 is a hand wash zone ID tag that includes a sensor suite for integrating multiple sensor functions. The sensor suite may include an RFID reader that identifies any entity ID tags 102 (e.g., health care worker ID tags or patient ID tags) that are in the hand wash zone associated with the hand wash zone ID tag. The sensor suite may also include a display (liquid crystal display or "LCD", light emitting diode or "LED", etc.) that indicates which identified health care worker or patient ID tag is the preferred entity ID tag (determined by order of entry, signal strength, or some other algorithm). The preferred entity ID tag is the ID tag of the health care worker or patient given credit by the hand hygiene compliance system for the hand washing or hand sanitizing event. If the cleanser is a sanitizer in a dispenser, then the sensor suite may receive an input from the dispenser that indicates that the sanitizer has been dispensed. If the hand wash zone ID tag is associated with a sink, the sensor suite may receive an input from the sink indicating that water is flowing and an elapsed time of the water flow. The sensor suite may also receive inputs from a soap dispenser when soap is dispensed and from a towel dispenser when a towel is dispensed.

In some embodiments, if the sensor suite determines that the water, soap, and towel inputs meet a predefined (and programmable) criteria, then the hand wash zone ID tag sends the unique identifier associated with the preferred ID tag and the unique identifier associated with the hand wash zone ID tag to a data collection device (e.g., central computer, synchronizing station, or entity ID tag) with an indication of a successful (or compliant) hand wash. Examples of the predefined criteria include, but are not limited to, a number of minutes that the water was run, an amount of soap that was dispensed, a number of times that soap was dispensed, a number of towels used, and an elapsed time that an electric hand dryer was run. The sensor suite (or other location in the hand wash zone) may also display an indication of a successful hand wash, or hand wash compliance, by displaying the unique identifier associated with the preferred entity ID tag and optionally a message indicating compliance. Alternatively, if the sensor suite determines that the water, soap, and/or towel inputs did not meet the predefined criteria, then the hand wash zone ID tag sends the unique identifier associated with the preferred entity ID tag and the unique identifier associated with the hand wash zone ID tag to a data collection device with an indication of an unsuccessful hand wash. In an embodiment, the sensor suite (or other location in the hand wash zone) also displays an indication of an unsuccessful hand wash by displaying the unique identifier associated with the preferred entity ID tag (or name of the health care worker or patient) and a message indicating that the hand wash was unsuccessful and, in some cases, suggested steps to complete a successful hand wash.

Figure 2:
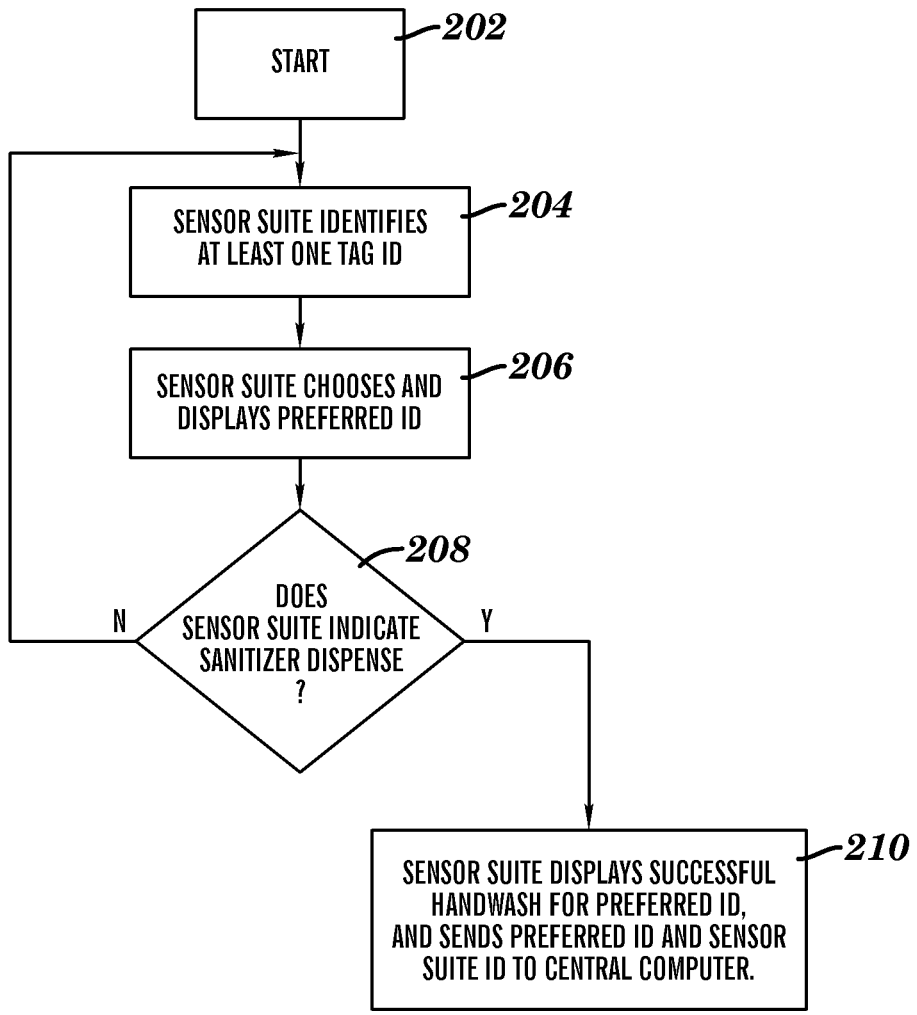
FIG. 2 depicts a process flow of determining hand-sanitizing activity in accordance with an embodiment.

FIG. 2 depicts a process flow of a hand wash zone sensor suite for a hand sanitizing event at a hand washing station that includes a dispenser for dispensing a sanitizing gel (or other sanitizing liquid) in accordance with an embodiment. Processing starts at block 202, followed by block 204, where the sensor suite identifies at least one entity ID tag 102 in the hand wash zone. At block 206, the sensor suite chooses and optionally displays (e.g., on a display at the hand washing station) a preferred entity ID tag 102 or other identifier. The sensor suite selects the preferred entity tag ID using an algorithm based on items such as, but not limited to, order of entry to the hand wash zone and/or signal strength of the entity ID tag. At block 208, it is determined if the sensor suite indicates that that the sanitizer was dispensed. Optionally, the sensor suite also indicates an amount of sanitizer that was dispensed. If the sanitizer was not dispensed (or alternatively, if less than a programmable pre-defined amount of the sanitizer was dispensed), then processing returns to block 204. If the sanitizer was dispensed, then processing continues at block 210 and the sensor suite displays (e.g., at the hand washing station and/or on the entity ID tag) a successful hand wash indicator for the preferred ID tag. In an embodiment, if the sanitizer was dispensed, but it was less than the programmable predefined amount, then processing continues at block 204. In an embodiment, the sensor suite sends the unique identifier associated with the preferred ID tag and the unique identifier associated with the hand wash zone ID tag, along with an optional timestamp, to a data collection device such as central computer 110. In another embodiment, the sensor suite sends the unique identifier associated with the preferred entity ID tag to the hand wash zone ID tag, which relays the unique identifier associated with the preferred ID tag and the unique identifier associated with the hand wash zone ID tag to the data collection device.

Figure 3:
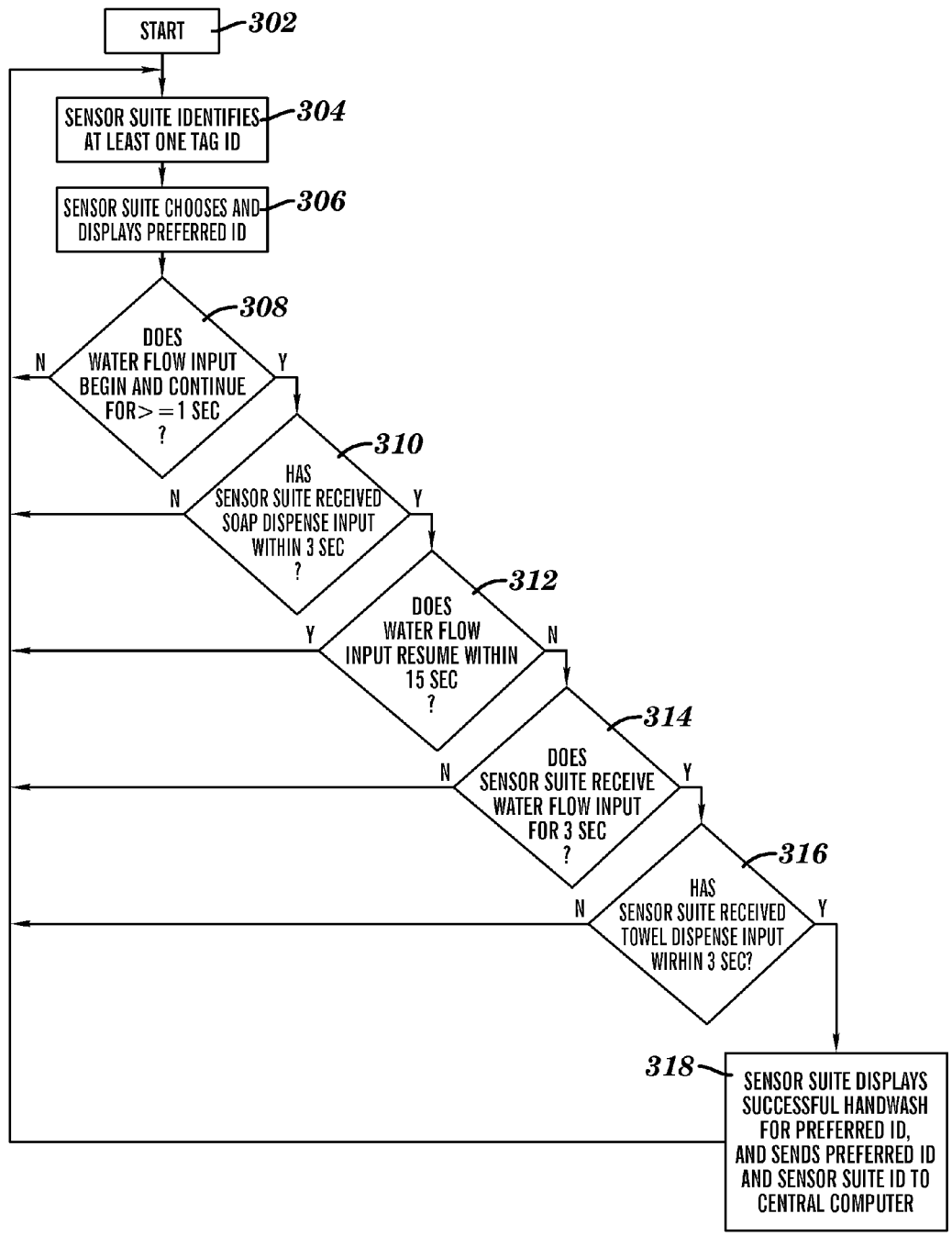
FIG. 3 depicts a process flow of determining hand washing activity in accordance with an embodiment.

FIG. 3 depicts a process flow of a hand wash zone sensor suite for a hand sanitizing event at a hand washing station that includes a sink for dispensing water, a soap dispenser for dispensing soap, and a towel dispenser for dispensing towels in accordance with an embodiment. Processing starts at block 302, followed by block 304, where the sensor suite identifies at least one entity ID tag 102 in the hand wash zone. At block 306, the sensor suite chooses and optionally displays (e.g., on a display at the hand washing station) a preferred entity ID tag 102. The sensor suite selects the preferred entity tag ID using an algorithm based on items such as, but not limited to, order of entry to the hand wash zone and signal strength of the entity ID tag. At block 308, it is determined if the water has been flowing at the sink for more than a predefined (and programmable) period of time (in this example one second). If the water has been flowing for more than the predefined period of time, then processing continues at block 310, otherwise processing returns to block 304. At block 310, it is determined if the sensor suite has received an indication that the soap dispenser is dispensing soap within in a preceding predefined (and programmable) number of seconds (in this example, three seconds). If the sensor suite has received an indication that the soap dispenser has dispensed soap within the predefined number of seconds, the processing continues at block 312, otherwise processing returns to block 304.

At block 312 in FIG. 3, it is determined if the water flow at the sink has resumed within a preceding predefined (and programmable) number of seconds (in this example, fifteen seconds). If the water flow has resumed within the preceding predefined number of seconds, then processing continues at block 314, otherwise processing returns to block 304. At block 314, it is determined by the sensor suite if the water has been flowing at the sink for more than a predefined (and programmable) period of time (in this example three seconds). If the water has been flowing for more than the predefined period of time, then processing continues at block 316, otherwise processing returns to block 304. At block 316, it is determined if the sensor suite has received an input from the towel dispenser indicating that that the towel dispenser has been used within a preceding predefined (and programmable) number of seconds (in this example, three seconds). If the sensor suite has received towel dispense input within the predefined number of seconds, then processing continues at block 318, otherwise processing returns to block 304. At block 318, the sensor suite optionally displays an indication of a successful hand wash by displaying the unique identifier associated with the preferred entity ID tag. In an embodiment, the sensor suite sends the unique identifier associated with the preferred entity ID tag and the unique identifier associated with the hand wash zone ID tag to a data collection device. In another embodiment, the sensor suite sends the unique identifier associated with the preferred entity ID tag to the hand wash zone ID tag, which relays it along with unique identifier associated with the hand wash zone ID tag to the data collection device.

The process flows shown in FIGS. 2 and 3 are examples of process that may be implemented by exemplary embodiments that utilize sensor suites. Multiple other configurations may also be implemented in accordance with exemplary embodiments and specific protocols being monitored. For example, a process that does not include block 308 of FIG. 3 is implemented for a hand hygiene protocol that does not require health care workers to have wet hands before applying soap. As another example, a process that does not include block 312 may be implemented for a hand hygiene protocol that does not require the water to be turned off while applying soap. As will be appreciated by those skilled in the art, numerous variations on content and order of processing blocks may be implemented by exemplary embodiments.

Figure 4:
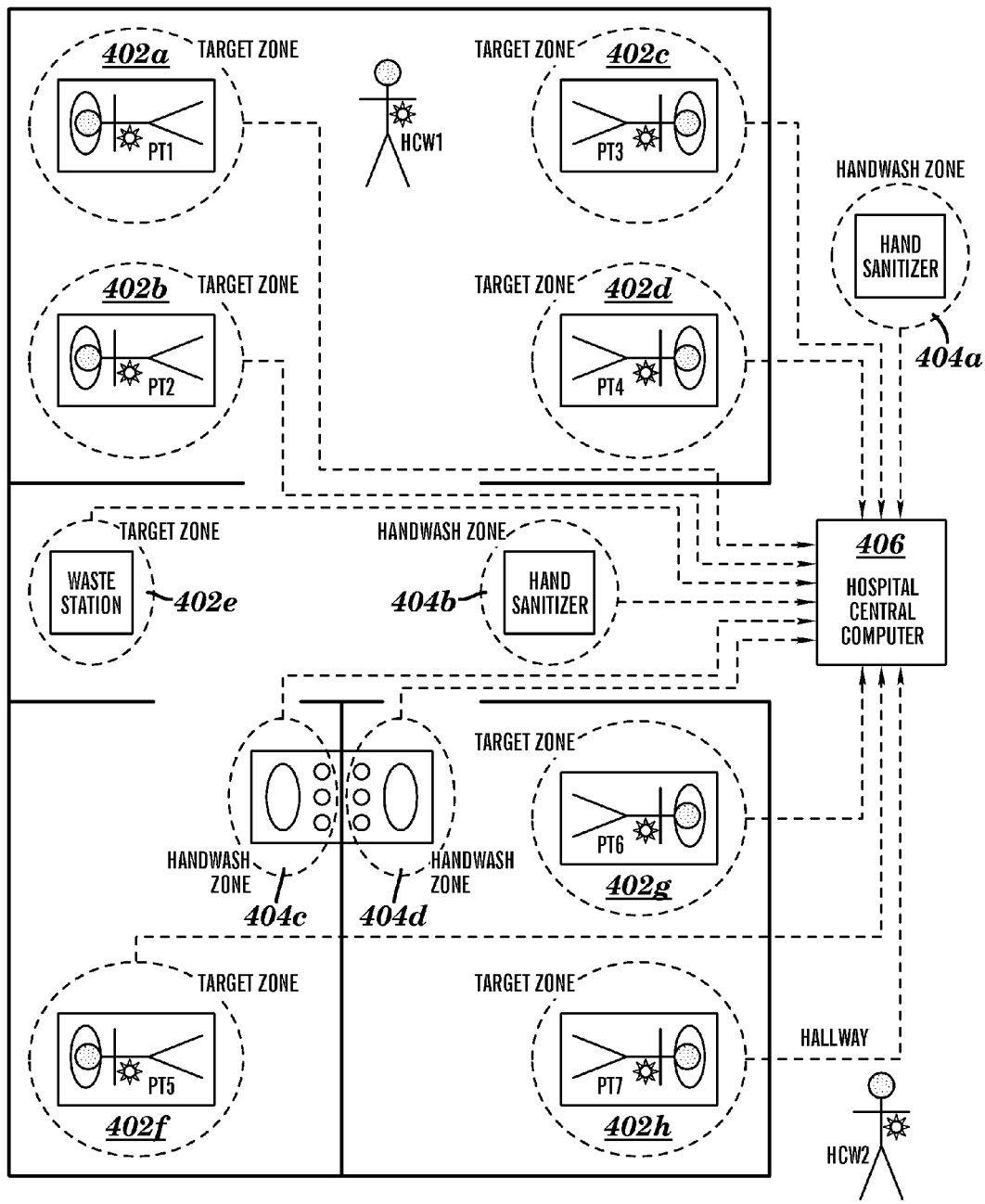
FIG. 4 depicts a hospital layout in accordance with an embodiment.

FIG. 4 depicts an embodiment of a hospital layout that includes target zones 402 and hand wash zones 404 that are in communication with a central computer 406. Target zones 402a-d and target zones 402f-h are target zones located around patient beds, and in this example all of the beds contain patients wearing patient ID tags with unique identifiers PT1-PT7. Target zone 402e is a target zone around a waste station. Hand wash zones 404a-b include hand sanitizer dispensers, and hand wash zones 404c-d include sinks/soap dispensers. As described previously, each target zone and hand wash zone includes a zone ID tag. As shown in FIG. 4, when a health care worker (e.g., HCW1 or HCW2) wearing a health care worker ID tag is within any of the target zones or hand wash zones shown in FIG. 4, a reader device within the zone receives a signal from the health care worker ID tag and records the presence of the health care worker in the corresponding zone. The unique identifier of the health care worker, the unique identifier of the zone, and optionally a time stamp is sent from each zone that detects an entity to the central computer 406 for storage and for reporting compliance with hand hygiene protocols. Additionally, the presence of a patient ID tag in a target zone 402 may be used to determine if the corresponding zone is active or not active.

Figure 5:
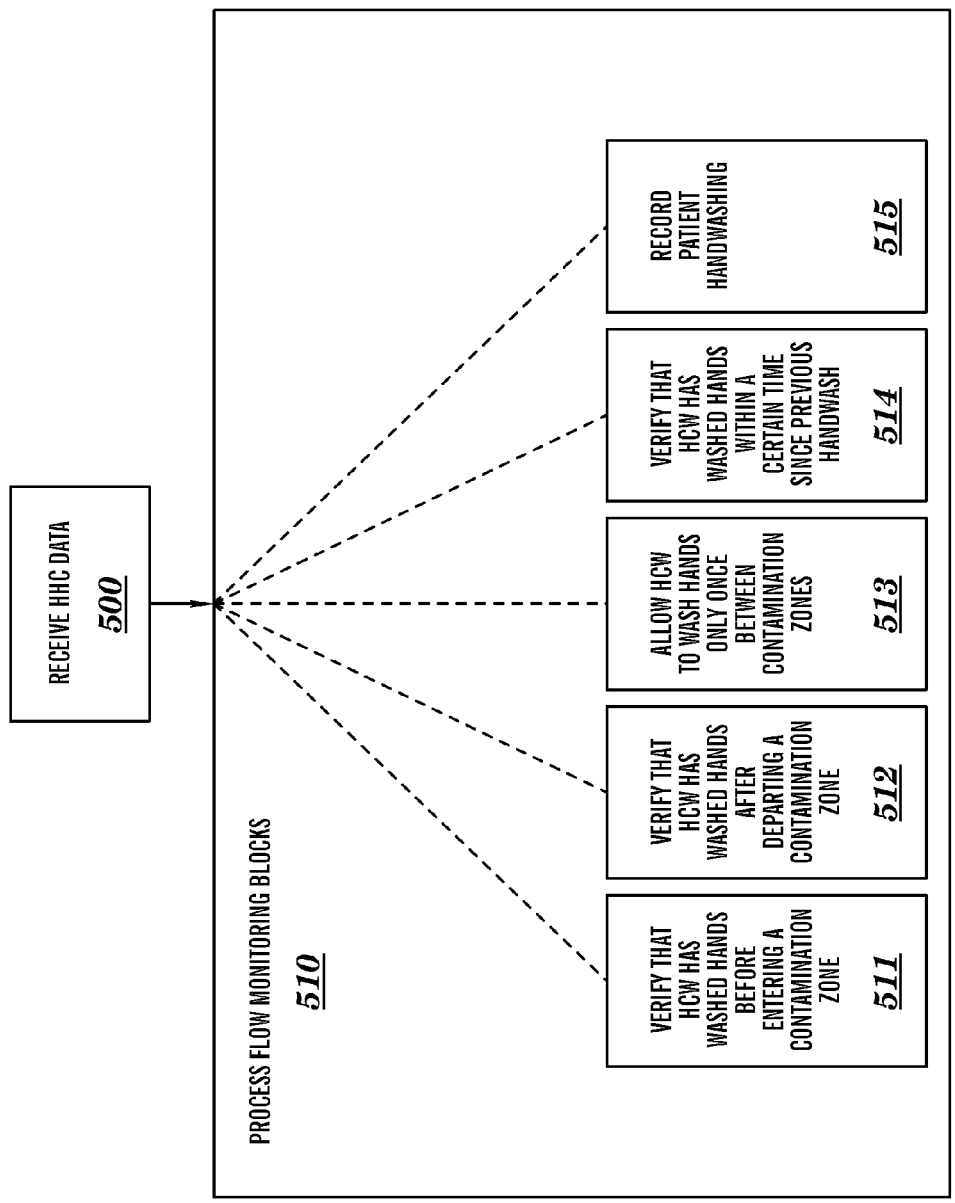
FIG. 5 depicts a high level process flow of a central computer hand hygiene compliance monitoring application in accordance with an embodiment.

FIG. 5 depicts a high level process flow of a central computer hand hygiene compliance monitoring application in accordance with an embodiment. In an embodiment, all or a subset of the blocks 511, 512, 513, 514, and 515 are performed in response to receiving hand hygiene compliance data. These blocks contain various criteria that are applied to determine whether a sanitation protocol has been flowed. The criteria are based on factors that include a current zone location of an entity, and may include one or more previous zone locations of an entity and approved hand washing zones for particular target zones. Whether a particular block is performed may depend on the hand hygiene compliance data received, other blocks performed, previously received data, and/or whether an authorized user device 108 has configured the hand hygiene compliance monitoring application 110 to perform the block. At block 500, the central computer receives hand hygiene compliance data from one or more zone ID tags. At block 510, hand hygiene compliance data (a type of sanitation compliance data) may be processed by all or a subset of the blocks 511 through 515, in any order. At block, 511, the hand hygiene compliance monitoring application verifies that a health care worker washed their hands at an approved hand wash zone before approaching a target zone (e.g., a target zone that includes a patient ID tag). In an embodiment, this occurs at the central computer when a target zone ID tag reports a detected health care worker ID tag to the computer. The hand hygiene compliance monitoring application executing on the central computer verifies that a patient occupies the same target zone, and the computer recalls prior hand washing events and/or contamination exposure events of the health care worker. The application then determines whether the most recent recorded activity of the health care worker was a hand wash at an approved hand wash zone (compliant), and updates compliance information in a database.

At block 512, the hand hygiene compliance monitoring application verifies that hand washing occurred at an approved hand washing zone after leaving an active target zone. When a target zone ID tag or hand wash zone ID tag (or associated sensor suite) reports a detected health care worker ID tag to the computer, the hand hygiene compliance monitoring application executing on the central computer recalls prior hand washing events and/or contamination exposure events of the health care worker. The application determines whether a health care worker's most subsequent recorded activity after a previous exposure to a target zone was a hand wash at an approved hand wash zone (compliant), and updates compliance information in a database.

Some hand hygiene protocols may require health care workers to wash their hands twice after departing one target zone and before entering the next target zone, while it may not be necessary to wash hands twice in other circumstances. For example, two hand washes may be required when moving from a waste station to a patient, and only one hand wash may be required when moving from one patient to another patient. At block 513, the hand hygiene compliance monitoring application determines whether circumstances required the health care worker to wash their hands twice. This is performed when a target zone ID tag (or associated sensor suite) reports a detected health care worker tag to the computer. If the protocol being enforced only requires hand washing once, then the computer does not report non-compliance to the database if the health care worker failed to wash their hands twice.

At block 514, the hand hygiene compliance monitoring application verifies that hand washing has occurred within a predefined (and programmable) elapsed time. When a hand wash zone ID tag (or associated sensor suite) reports to the computer that the a health care worker is in the hand wash zone (or in the case of a sensor suite that that patient has performed a successful hand wash), the application can determine whether the elapsed time since a previous hand wash by the health care worker is greater than the maximum allowed time between successive hand washings. If so, the health care worker is non-compliant.

At block 515, the hand hygiene compliance monitoring application records patient hand washing. When a hand wash zone ID tag (or associated sensor suite) reports to the computer that a patient is in the hand wash zone (or in the case of a sensor suite that the patient has performed a successful hand wash) this data is saved to a database. The hospital can utilize this information to help track the containment of contamination.

Figure 6A:
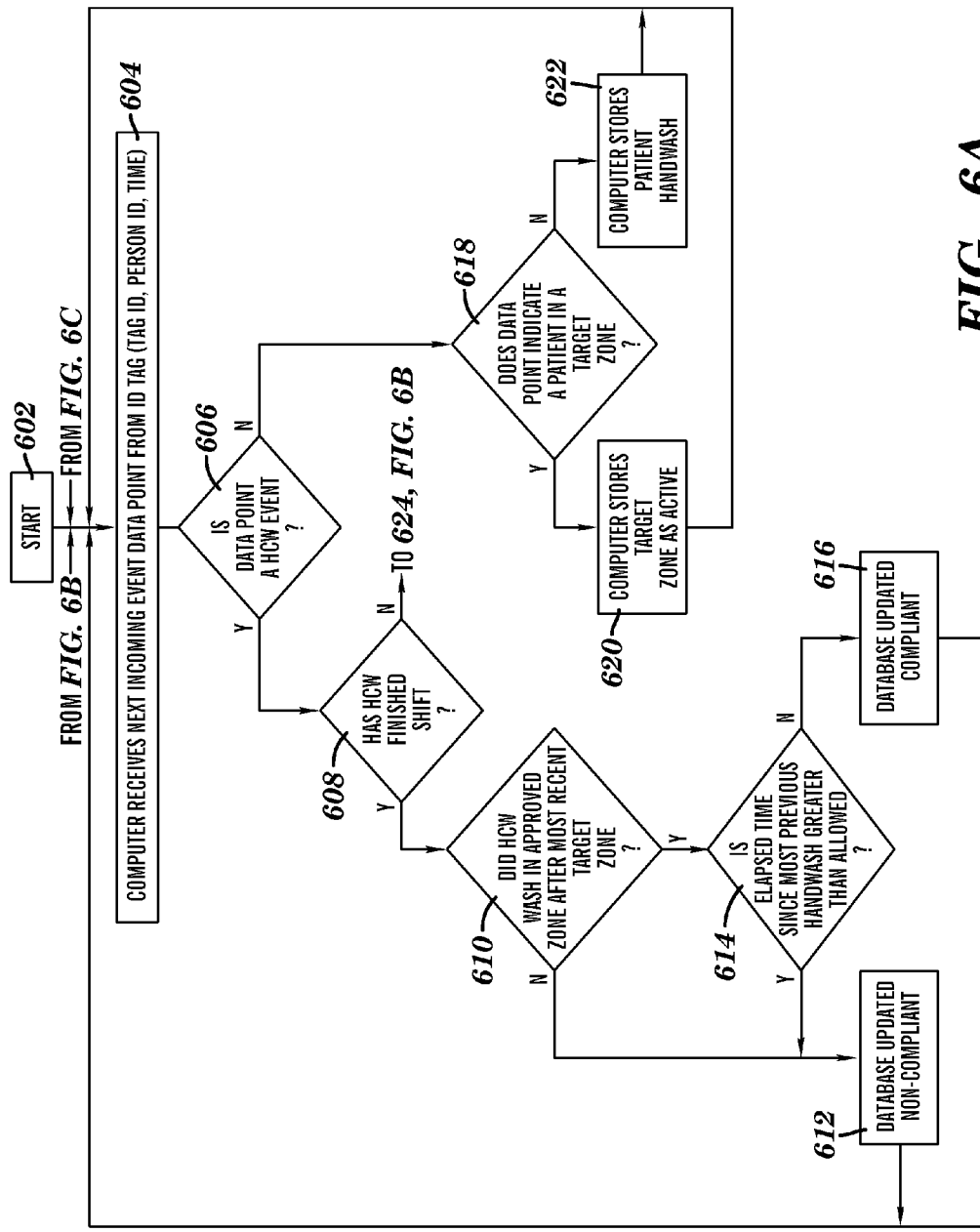
FIGS. 6A, 6B and 6C, depicts a more detailed view of the process flow of FIG. 5 in accordance with an embodiment.
Figure 6B:
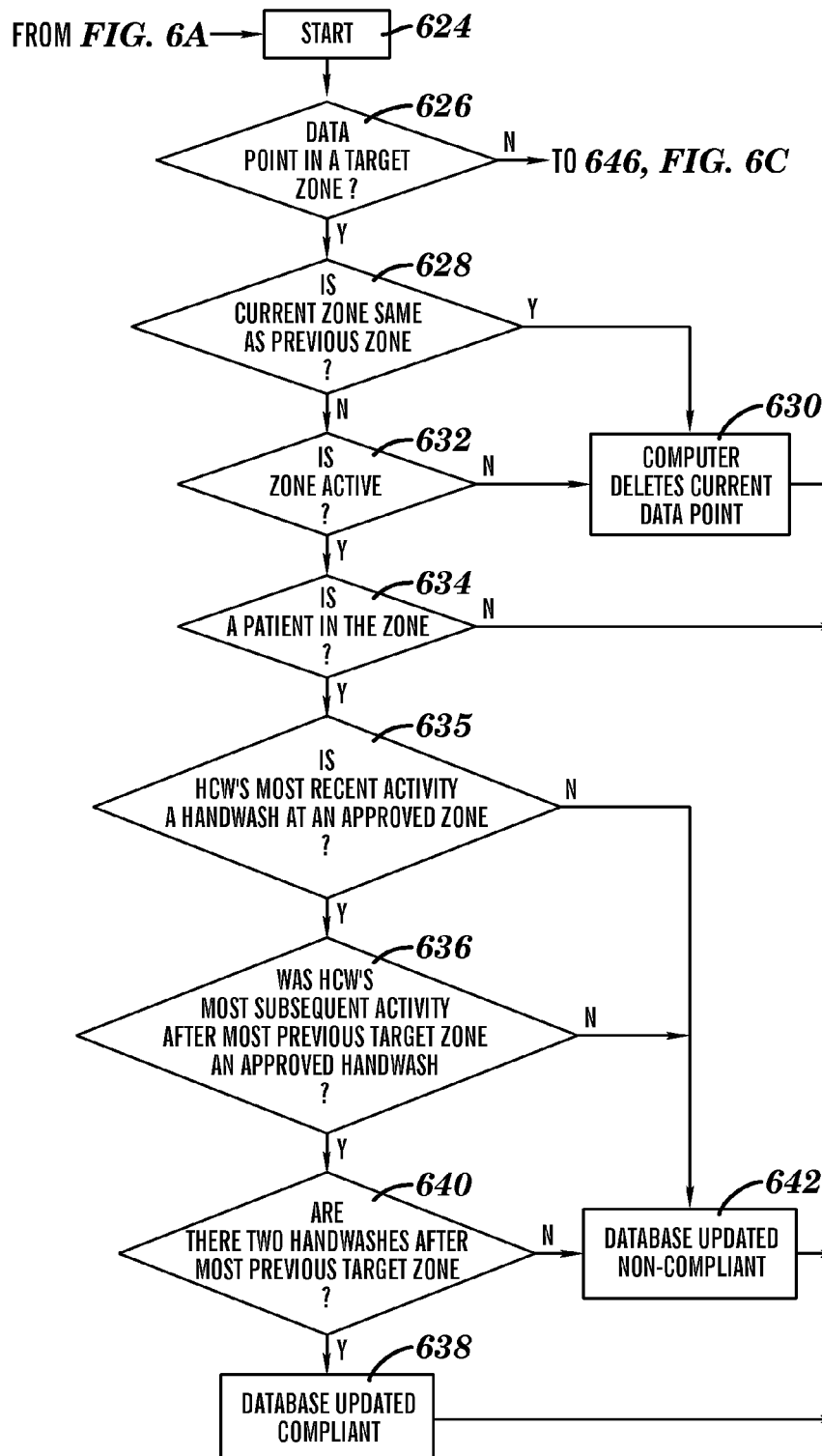
Figure 6C:
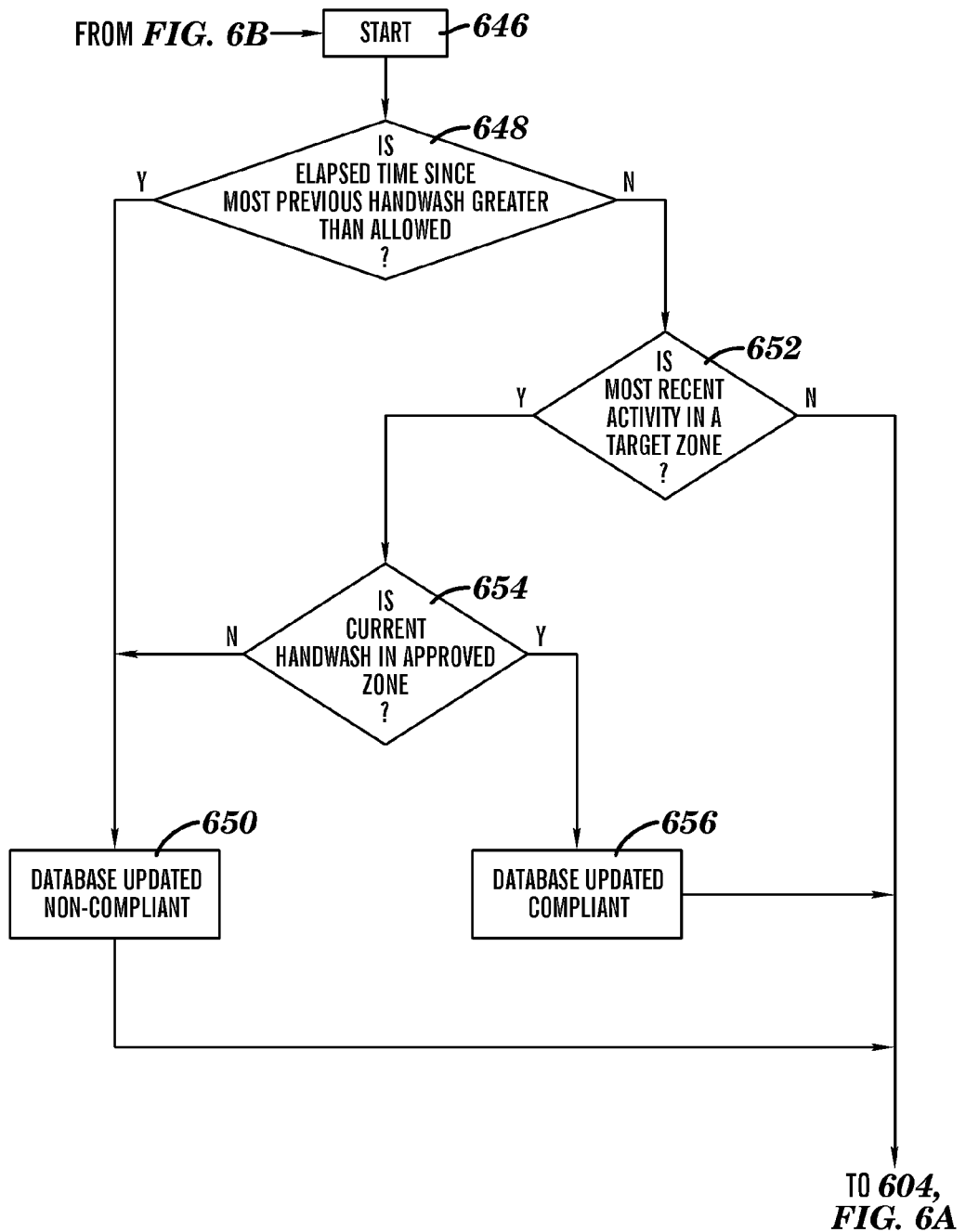

FIG. 6, which includes FIGS. 6A-6C, depicts one embodiment of a process flow that may be implemented by the hand hygiene compliance monitoring application to perform the high level process flow shown in FIG. 5 in accordance with an embodiment. The process starts at block 602 and continues at block 604 where a next incoming event data point (a type of sanitation compliance data) is received by the computer from a reader device (or synchronization device). The data point includes a unique identifier associated with an entity ID tag, a unique identifier associated with a zone ID tag, and optionally a timestamp. At block 606, it is determined if the entity ID tag is a health care worker ID tag. If it is not (i.e., the entity ID tag is patient ID tag), then processing continues at block 618 to determine if the data point indicates that a patient is in a target zone. The data point indicates that the patient is in a target zone if the zone ID tag is associated with a target zone. If the data point indicates that a patient is in the target zone, then processing continues at block 620, where the computer stores, in a database, an indication that the target zone is active (because it contains a patient). Otherwise, processing continues at block 622, where the computer stores, in the database, an indication that the patient has performed a hand wash (i.e, the zone ID tag is associated with a hand wash zone).

If it is determined at block 606, that the data point is a health care worker event then processing continues at block 608, where it is determined whether the health care worker has finished a work shift. If the health care worker has finished a work shift, then processing continues at block 610 to determine whether the health care worker washed in an approved hand wash zone after the health care worker left the last target zone. If it is determined that the health care worker had washed in an approved hand wash zone, processing continues at block 614, where it is determined if the elapsed time since the most recent hand wash of the health care worker is greater than a predefined (and programmable) time. If the elapsed time since the most recent hand wash of the health care worker is not greater than the predefined time, then processing continues at block 616 where the health care worker is indicated in the database as being compliant. In an embodiment, the indication of compliant includes the unique identifier associated with the health care worker ID tag, the unique identifier associated with the target zone ID tag and a time stamp to indicate that as of the recorded time, the health care worker was compliant with the protocol. Processing then continues at block 604 to get the next data point.

If it is determined at block 610 that that the health care worker did not perform a hand wash in an approved hand wash zone after exiting the last target zone, then processing continues at block 612 where the database stores an indication of non-compliance for the health care worker. In an embodiment, the indication of non-compliance includes the unique identifier associated with the health care worker ID tag, the unique identifier associated with the target zone ID tag and a time stamp to indicate that as of the time indicated by the time stamp, the health care worker was not compliant with the protocol. Processing then continues at block 604 to get the next data point.

If it is determined at block 608, that the health care worker has not finished a shift, then processing continues at block 624 in FIG. 6B, followed by block 626. At block 626, it is determined if the data point associated with the health care worker is in a target zone. If the data point is in a target zone, then processing continues at block 628 to determine if the target zone recorded for the health care worker is the same as the previous target zone recorded for the health care worker. If they are the same, then the health care worker has not moved to a different target zone and processing continues at block 630 to delete the current data point. If the target zone is not the same as the previous target zone for the health care worker, then processing continues at block 632 to determine if the target zone is active. If the target zone is not active, then activity in this inactive target zone does not need to be tracked and processing continues at block 630 to delete the current data point, followed by a return to block 604 in FIG. 6A. At block 634, it is determined if there is a patient in the zone. If there is not a patient in the target zone, then processing continues at block 604 in FIG. 6A. Otherwise processing continues at block 635.

At block 635, it is determined if the health care worker's most recent activity was a hand wash at an approved hand wash zone. If it was, then processing continues at block 636 to determine whether the health care worker moved right from a target zone into an approved hand wash zone. If the health care worker moved directly from a target zone into an approved hand wash zone, then processing continues at block 640 where it is determined whether two hand washes are recorded for the health care worker after the health care worker was in a target zone. If two hand washes were recorded, then processing continues at block 638 with the database recording an indication of compliant for the health care worker. Processing then continues at block 604 in FIG. 6A. If any of blocks 635, 636 or 640 do not hold true, then processing continues at block 642, with the database recording an indication of non-compliant for the health care worker, followed by returning to block 604 in FIG. 6A to get another data point.

If it is determined at block 626 in FIG. 6B that the data point is not from a target zone (i.e., it is from a hand wash zone), then processing continues at block 646 in FIG. 6C. Block 646 is followed by block 648, where it is determined if an elapsed time since a most previous hand wash activity by the health care worker is greater than a predetermined (and programmable) threshold. If it is not, then processing continues at block 652 where it is determined whether the most recent activity associated with the health care worker is in a target zone. If the most recent activity is within a target zone, then processing continues at block 654 where it is determined whether the current hand wash is at an approved hand wash zone. In an embodiment, an approved hand wash zone is generally in close proximity to the previous target zone, indicating that the health care worker has performed a hand wash close to any possible contamination. If the current hand wash zone is an approved hand wash zone, then block 656 is performed to update the database to indicate that the health care worker is complaint, and processing continues at block 604 in FIG. 6A. If it is determined at block 648 that the elapsed time since the most previous hand wash is greater than a threshold, or it is determined at block 654 that the current hand wash is not in an approved hand wash zone, then processing continues at block 650 with the database storing an indication that the health care worker is not compliant with the hand wash protocol. Processing then continues at block 604 in FIG. 6A.

The process flows shown in FIGS. 5 and 6 are examples of two processes that may be implemented by exemplary embodiments to determine compliance and non-compliance with an example hand hygiene protocol. The blocks may be different and/or in a different order depending on the particular hand hygiene protocol being implemented by an embodiment. Thus, multiple other processes may also be implemented in accordance with exemplary embodiments. In one alternate embodiment, entity ID tags only include health care worker ID tags, and patient ID tags are a type of zone ID tag. In this embodiment, the patient ID tags are worn by the patients resulting in a target zone around each patient. For this embodiment, blocks 632 and 634 of FIG. 6B are replaced with one decision block to determine if the zone ID tag is associated with a patient zone. Block 636 is performed if the zone ID tag is associated with a patient zone, and block 604 in FIG. 6A is performed otherwise.

Table 1 below depicts a scenario in which the hand hygiene compliance with a protocol, such as that shown in FIGS. 4-6 above, is monitored for a health care worker (in this example HCW2). In this example, all beds shown in FIG. 4 begin with patients occupying them except for the one corresponding to target zone 402a, and the hospital only allocates one approved hand wash zone per target zone 402. In this example, hand wash zone 404b is the approved hand wash zone for target zones 402a-d; hand wash zone 404c is the approved hand wash zone for target zone 402f; hand wash zone 404d is the approved hand wash zone for target zones 402g-h; and hand wash zone 404b is the approved hand wash zone for target zone 402e. In addition, every health care worker must wash their hands at least once every sixty minutes. Referring to Table 1 below, the first column is a timestamp, the second column includes a data point and the third column shows data written to a database by the hand hygiene compliance monitoring application for the health care worker in response to the data points in accordance with an embodiment.

TABLE 1

| Time | Data Point | Hand Hygiene Compliance Application Action |
|---|---|---|
| 1:00 | Begins shift, sanitizes at 404a | None |
| 1:05 | Sanitizes at 404b | None |
| 1:10 | Enters 402a | Deletes data point. |

TABLE 1-continued

| Time | Data Point | Hand Hygiene Compliance Application Action |
|---|---|---|
| 1:15 | Enters 402b | COMPLIANT ID tag, approved hand wash before patient |
| 1:20 | Patient departs 402b, HCW2 remains in 402b | Deletes data point (but has retained initial contact in 402b) |
| 1:25 | Enters 402e | None |
| 1:30 | Sanitizes at 404b | COMPLIANT ID tag approved hand wash after target zone |
| 1:35 | Enters 402g | NON-COMPLIANT ID tag, no approved hand wash before patient. NON-COMPLIANT ID tag, didn't wash twice before patient |
| 1:40 | Enters 402h | NON-COMPLIANT ID tag, no approved hand wash before patient. NON-COMPLIANT ID tag, no approved hand wash after previous target zone |
| 3:00 | Sanitizes at 404a | NON-COMPLIANT ID tag, more than 60 minutes since last hand wash |
| 3:05 | Washes at 404c | None |
| 3:10 | Enters 402f | COMPLIANT ID tag, approved hand wash before patient NON-COMPLIANT ID tag, no approved hand wash after previous target zone |
| 3:15 | Washes at 404c | COMPLIANT ID tag, approved hand wash after target zone |
| 4:00 | Washes at 404d | None |
| 4:30 | Enters 402g | COMPLIANT ID tag, approved hand wash before patient |
| 4:40 | Washes at 404d | COMPLIANT ID tag, approved hand wash after target zone |
| 4:45 | Enters 402h | COMPLIANT ID tag, approved hand wash before patient. NON-COMPLIANT ID tag, didn't wash twice before patient. |
| 5:00 | Sanitizes at 404a | None |
| 6:30 | Ends shift. | NON-COMPLIANT ID tag, no approved hand wash after previous target zone 2) NON-COMPLIANT ID tag, more than 60 minutes since last hand wash |

Other embodiments includes a distributed implementation of the hand hygiene compliance monitoring system, where passive RFID tags, active RFID tags, other RF transceivers, or RF beacons are mounted in target zones and hand wash zones, and a health care worker ID tag in the form of an RFID reader is worn by one or more of the health care workers. If the health care worker ID tag detects a signal from a target zone or hand wash zone, the health care worker ID tag stores the target zone ID or hand wash zone ID temporarily in memory located on the health care worker ID tag. In accordance with an embodiment, from time to time (depending upon location, time limits, and/or other specified limits set by the hand wash compliance system administrator) the RFID reader ID tag transmits a wireless signal in an attempt to connect with a network connection or "synchronizing station" and, once connected, wirelessly uploads to the synchronizing station any information (such as target zone or hand wash zone events) stored in the health care worker ID tag. In another embodiment, a synchronizing station is continuously transmitting a wireless signal in an attempt to connect with the health care worker ID tag, and once connected, the health care worker ID tag wirelessly uploads to the synchronizing station any information (such as target zone or hand wash zone events) stored in the health care worker ID tag. In a further embodiment, from time to time, the health care worker ID tag and synchronizing station are physically connected, perhaps with a wire, to upload to the synchronizing station any information (such as target zone or hand wash zone events) stored in the health care worker ID tag. In these embodiments, the synchronizing station relays information from the health care worker ID tag to the computer monitoring the hand washing compliance system.

These "synchronizing station" embodiments, use essentially the same compliance determination logic described previously. The differences are in the entity ID tags, zone determinations, and how data is transmitted to the hospital's central computer to determine hand hygiene compliance. The advantages include reducing the overall number of RFID readers in the compliance system, and reducing or eliminating the need to connect to a LAN infrastructure in a hospital, or other facility.

Figure 7:
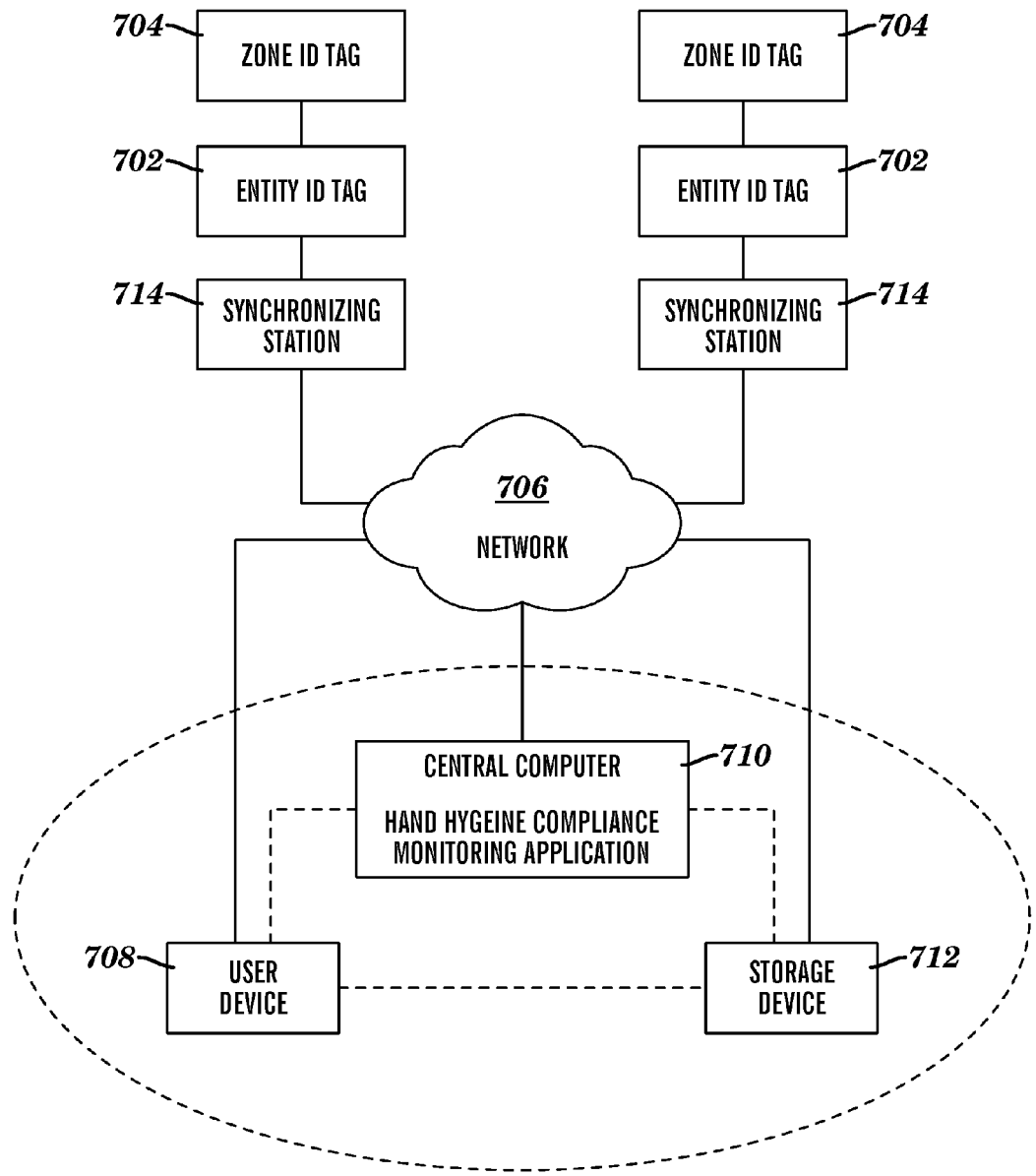
FIG. 7 depicts a distributed hand hygiene compliance system in accordance with an embodiment in which synchronization stations are utilized to collect compliance data.

FIG. 7 depicts a distributed hand hygiene compliance system implemented in accordance with an embodiment. The system depicted in FIG. 7 includes a plurality of synchronization stations 714 in communication with central computer 710 via a network 706 for transmitting data to a hand hygiene compliance monitoring application executing on the central computer 710. The synchronization stations 714 gather data from RFID readers or other radio frequency transceivers located on entity ID tags 702. The entity tags 702 gather data from radio frequency beacons, passive RFID tags, active RFID tags, or other radio frequency transceivers located on zone ID tags 704. In an embodiment, the synchronization stations 714 collect the data when an entity (such as a health care worker or a patient) comes within range to communicate information with a synchronization station 714. In an embodiment, the network 706 is implemented by a LAN. It will be appreciated that network 706 can be implemented using other types of wired and wireless networks such as, but not limited to the Internet, and an intranet. As depicted in FIG. 7, network 706 is in communication with the central computer 710, a storage device 712, and a user device 708.

The user device 708 depicted in FIG. 7 is utilized to access the hand hygiene compliance monitoring application executing on the central computer 710. In an embodiment, the hand hygiene compliance monitoring application 710 includes software instructions to receive data from the synchronizing stations 714 and to perform functions described herein related to monitoring hand hygiene compliance.

Figure 8A:
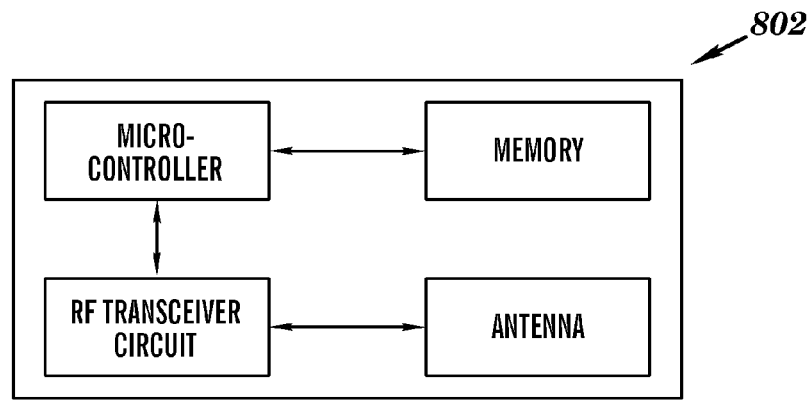
FIGS. 8A and 8B, depicts active radio frequency identification (RFID) reader badges in accordance with embodiments.
Figure 8B:
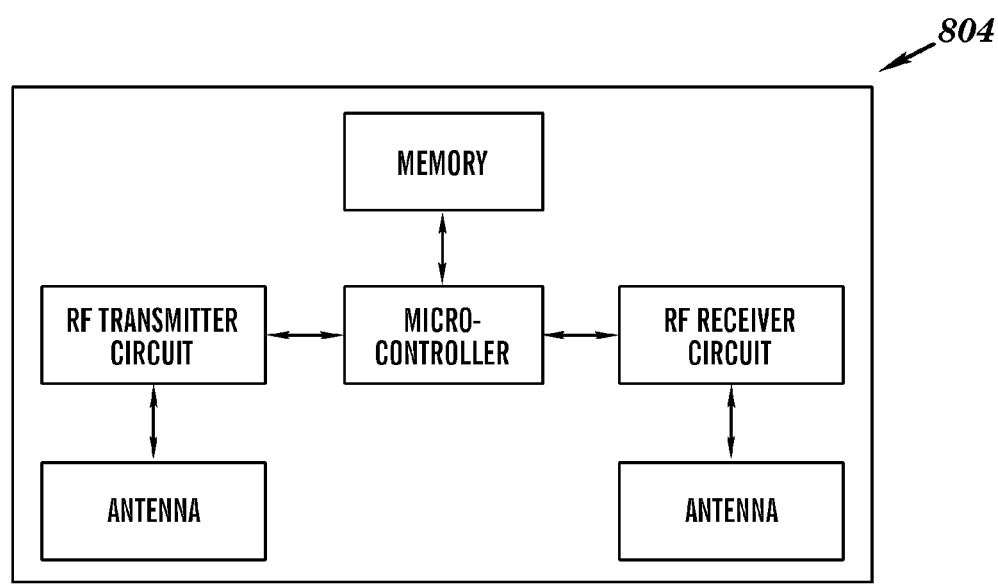

Referring now to FIG. 8, which includes FIGS. 8A-8B, embodiments of transceiver ID tags that may used for the entity ID tags described above with respect to FIG. 7 are generally shown. In an embodiment, such as the one depicted in FIG. 8A, a radio frequency transceiver ID tag 802 is powered by a battery or other source and includes a microcontroller, a memory, a radio frequency transceiver circuit, and an antenna. In another embodiment, the radio frequency transceiver ID tag also includes a user interface to communicate (visual, audio, haptic) with the wearer of the ID tag (e.g., a health care worker) to provide, for example, information regarding compliance status. In an embodiment, the user interface is arranged to display and/or provide compliance status to any one interacting with the wearer or in the vicinity of the wearer.

The radio frequency transceiver circuit portions of the radio frequency transceiver ID tag 802 may be configured as shown in the embodiment of FIG. 8A with an radio frequency transceiver and circuit components responsible for both transmitting and receiving. In another embodiment, a radio frequency transceiver ID tag 804 can be configured as shown in the embodiment of FIG. 8B with a separate transmitter circuit and receiver circuit with some separate components (e.g., the receiver and transmitter have separate antennas). Both radio frequency transceiver ID tag 802 and radio frequency transceiver ID tag 804 are examples of ID tags (e.g., zone ID tag, entity ID tag).

An embodiment of a radio transceiver ID tag utilizes an electro-chemical cell as a battery. Other alternatives are utilized by other embodiments, including, but not limited to high value capacitors (e.g., "super" or "ultra" or "Aerogel" capacitors).

Embodiments are described herein that utilize RFID technology. Other embodiments utilize technologies that can be used to communicate wirelessly such as, but not limited to, wireless fidelity (WiFi); infrared communications; and ultra sonic communications. In another embodiment, Blue Tooth® technology is utilized.

An embodiment of the memory shown in radio frequency transceiver ID tags 802 and 804 is implemented using non-volatile memory such as, but not limited to electrically erasable programmable read only memory (EEPROM). The memory is used to keep a record of events that the wearer has initiated or participated in. The size of this memory may be dictated by factors such as number of zones, frequency of interactions with those zones, the update rate specified (that is the frequency of data collection), the amount of data required by the compliance system, and the length or duration between communicating information to a synchronizing station or other data collection device.

In an embodiment, the health care worker ID tag performs one or more of the following, signaling the ID tag (or badge) wearer if they are in compliance or not; signaling the ID tag wearer if they actually do not have to wash their hands; and signaling to other people in the vicinity of the ID tag wearer the compliance status of the ID tag wearer. The signaling may be performed using audio (e.g., specific sounds), visual (e.g., badge containing the ID tag blinks) and/or haptic (e.g., badge containing the ID tag vibrates).

In accordance with an embodiment, a zone is identified by a sensor suite that includes an ID tag. In an embodiment, the sensor suite collects data from the multiple components of, for example, a hand washing station (such as water on/off, water temperature, water flow rate, soap dispenser energized, towel dispenser energized) to determine if appropriate hand washing activity has taken place. In an embodiment, a sensor suite on a hand washing station may also identify ID tags within communication distance, select a preferred ID tag, display the preferred ID tag to which credit will be given for any hand washing activity, transmit the preferred ID tag number to a data collection device, display the ID tag number and other information on a screen, and communicate this information to the preferred ID tag.

Figure 9:
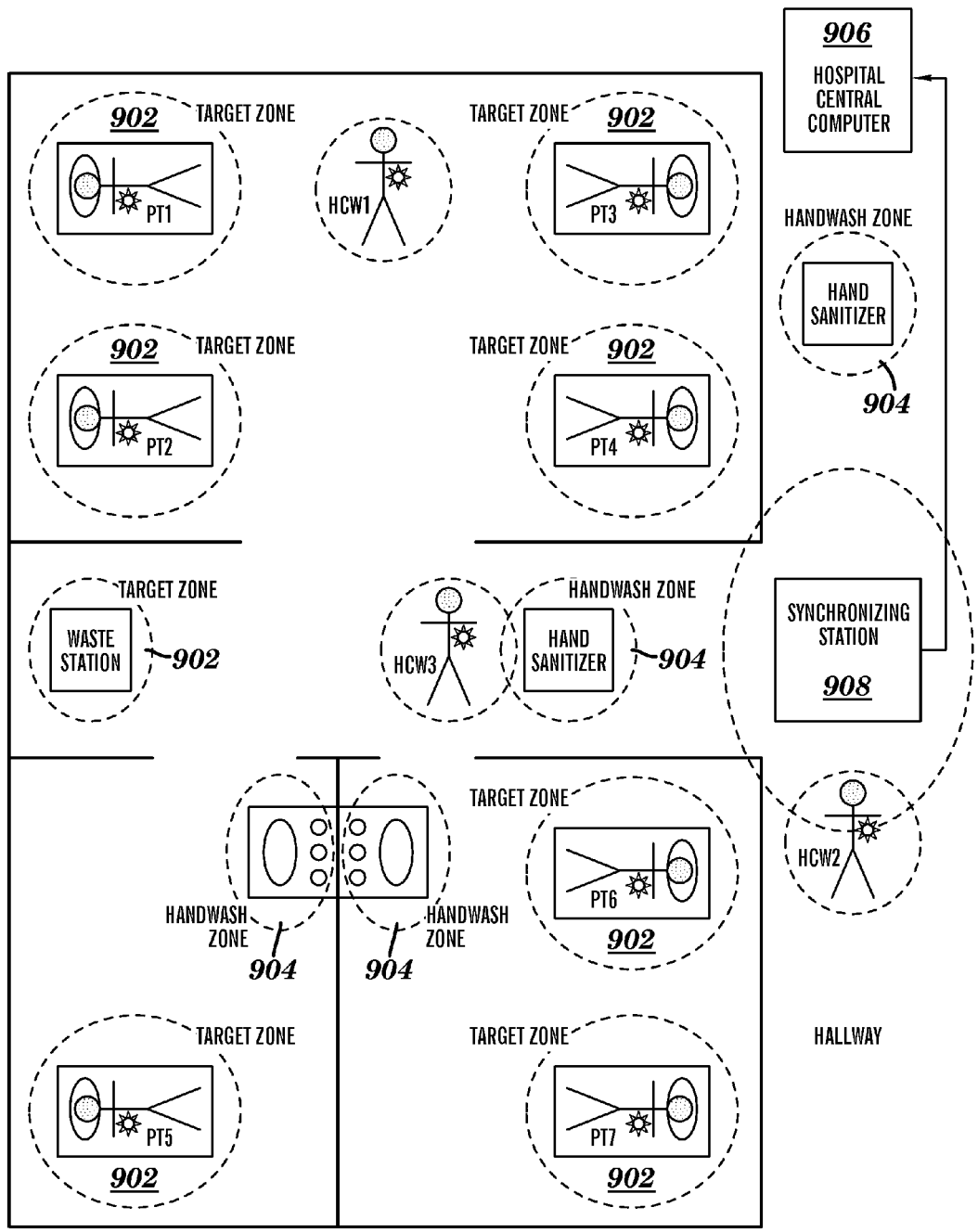
FIG. 9 depicts a hospital layout in accordance with an embodiment in which synchronization stations are utilized to collect compliance data.

FIG. 9 depicts a hospital layout in accordance with an embodiment where the health care worker ID tag is an RFID reader or other radio frequency transceiver capable of processing data, and synchronizing stations 908 are utilized to collect compliance data. The hospital layout shown in FIG. 9 includes target zones 902, and hand wash zones 904, as well as numerous patients (PT1-PT7) and three health care workers (HCW1-HCW3). As shown in FIG. 9, synchronizing stations, such as synchronization stations 714 or 908, are located at strategic locations in the hospital, such as exit doors, main corridors, etc. In an embodiment, synchronizing stations continuously transmit a wireless signal over a limited radius. If a health care worker ID, such as entity tag 702 or HCW2, receives the signal from a synchronizing station, the health care worker ID tag wirelessly transmits to the synchronizing station any information stored in the health care worker ID tag. The synchronizing station relays this information to the central computer 906. The hand hygiene compliance application processes this data as described previously herein to determine hand hygiene compliance.

In an embodiment, the health care worker ID tag is an RFID reader or other radio frequency transceiver that is continuously listening for signals from zone ID tags or synchronizing stations 714. If a signal from a zone ID tag is received, the health care worker ID tag stores the zone ID tag number as well as a time stamp. In an embodiment, the health care worker ID tag is an always-on RFID reader that continuously queries, listens for, and stores the unique identifiers of nearby passive RFID tags, active RFID tags, other radio frequency transceivers, and/or radio frequency beacons. In another embodiment, the health care worker ID tag is a radio frequency transceiver that listens for signals from zones or synchronizing stations, and the health care worker ID tag only broadcasts its own signal when transmitting its unique tag identifier and/or stored event information. In this embodiment, when the health care worker ID tag receives a signal that it is in a target zone, it stores the unique identifier of the target zone and a timestamp, and is thus not required to broadcast its presence to the zone ID tag. If the health care worker ID tag receives a signal that it is in a synchronizing station zone, it communicates its health care worker ID and any stored event history with the synchronizing station according to an embodiment. If the health care worker ID tag receives a signal that it is in a hand wash zone, or specifically a hand wash zone that includes a sensor suite, the health care worker ID tag broadcasts its health care worker ID periodically (a few times a second). In an embodiment, a health care worker ID tag in a hand wash zone broadcasts a confirmation that it received a "successful hand wash" signal from a hand wash zone ID tag or sensor suite so the hand wash zone ID or sensor suite can inform the health care worker that he has been credited.

In an embodiment, the patient ID tag is a passive or active RFID tag that transmits its own unique identifier in response to a query from a RFID reader or other radio frequency transceiver or radio frequency beacon. In another embodiment, the patient ID tag is an active tag that periodically transmits its own unique identifier over a limited radius without being queried.

In an embodiment, a target zone ID tag is a passive or active RFID tag that transmits its own unique identifier, and optionally a timestamp, in response to a query from a RFID reader or other radio frequency transceiver or radio frequency beacon. In another embodiment, the target zone ID tag is a radio frequency beacon, RFID reader, or other radio frequency transceiver that continuously broadcasts its own unique identifier over a limited radius without being queried. In an embodiment, the target zone ID tag is an RFID reader or other radio frequency transceiver that listens for radio signals such as those originating from nearby patient ID tags or health care worker ID tags. In an embodiment, the target zone ID tag responds to the presence of a health care worker ID tag or patient ID tag by transmitting at least one signal that indicates that a health care worker or patient is in the target zone. In an embodiment, the target zone ID tag stops transmitting a signal if a patient is not in the target zone (rendering the zone "inactive").

In another embodiment, the target zone ID tag is a radio frequency beacon that continuously transmits a two-item signal comprising its own unique identifier and an indication of whether a patient is present, the latter controlled by a manual toggle activated by an authorized health care worker, the patient, some other person, or some other non-human means (infrared detector, weight detector, etc.). An embodiment includes using a LED light, or other indicator, that illuminates if a patient is present, and/or illuminates in a different manner (e.g., a different color or blinking) if a patient is not present, to help remind health care workers whether they need to wash their hands or not.

In an embodiment, a hand wash zone ID tag is a passive RFID tag or active RFID tag that transmits its own unique ID in response by a query from an RFID reader or other RF transceiver or RF beacon. In an embodiment, a hand wash zone ID tag is an RF beacon that continuously transmits its zone ID over a limited radius. In an embodiment, a hand wash zone sensor suite receives signals from health care worker ID tags, displays a preferred health care worker ID tag ID, and detects whether sufficient inputs are received to indicate a successful hand wash. The hand wash zone ID tag transmits a signal to any listening health care worker ID tags that the health care worker associated with the preferred ID should be credited with a successful hand wash.

In an embodiment, at least one hand wash zone includes a sensor suite and a radio frequency transceiver that are powered by AC, batteries, or some other source. In an embodiment, the hand wash zone is the area in which a health care worker ID tag can detect a signal from the RF transceiver. In an embodiment, the radio frequency transceiver transmits a "talk" command four times per second (or at some other interval), requesting any listening health care worker ID tags to transmit their unique ID. The radio frequency transceiver listens for health care worker ID tag numbers, chooses a preferred ID, and causes a display to indicate the preferred ID. In an embodiment, the sensor suite receives input from at least one dispenser or other device and determines whether the input(s) indicate a successful hand hygiene event in a manner such as the shown in FIG. 2 or FIG. 3. If so, the radio frequency transceiver transmits its unique identifier and the unique identifier of the preferred health care worker. In an embodiment, the radio frequency transceiver listens for the preferred health care worker ID tag to transmit the hand wash zone ID as acknowledgement, and if acknowledged, causes a display to indicate that the preferred ID receives credit for the hand hygiene event.

In an embodiment, each synchronizing station includes an RF transceiver, memory, power source (likely AC), and data connection to the central computer (wired or wireless). In an embodiment, the RF transceiver transmits a "synchronize" command 4 times per second (or at some other regular interval) requesting any listening health care worker ID tags that have an event history stored in memory to transmit that data and their unique identifiers. If a synchronizing station receives a full event history from an health care worker ID tag, the synchronizing station transmits the event history to the central computer to determine hygiene compliance, and orders the health care worker ID tag to delete its memory according to an embodiment.

In an embodiment, patient ID tags are not required because patient target zones are activated manually. According to an embodiment, if the hospital wanted to determine patient hand washing and/or exposure to target zones, the hospital would need to issue patients the same type of badge that health care worker's use.

In a synchronizing station embodiment, the hand hygiene compliance monitoring application executing on the central computer determines hygiene compliance in a manner similar to that described above. In an embodiment, the central computer does not have to determine if a patient is present in a patient target zone. This is because the target zone radio frequency beacon or other radio frequency transceiver is deactivated or removed when a patient is not present, therefore the target zone cannot transmit its unique identifier to a health care worker ID tag for hand hygiene compliance determination.

The following table summarizes conditions and actions occurring at the different elements in a synchronizing station embodiment, such as that shown above in FIG. 7.

| Item | Description |
| --- | --- |
| Target Zone | 1) broadcasts unique identifier<br>2) manually enabled/disabled<br>3) displays red if enabled, green if disabled |
| Hand wash Zone | 1) broadcasts "talk" command<br>2) hears and chooses preferred HCW ID tag<br>3) displays preferred HCW ID tag unique identifier and any hand wash status<br>4) broadcasts unique identifier of hand wash zone to preferred HCW ID tag with hand wash status |
| Synchronizing Station | 1) broadcasts "synchronize" command<br>2) receives HCW ID tag identifier and event history<br>3) relays information to central computer<br>4) broadcasts "delete" command to HCW ID tag |
| HCW ID tag | 1) hears and stores zone event history<br>2) broadcasts its unique identifier if in hand wash zone<br>3) broadcasts its unique identifier and event history if in synchronizing zone<br>4) deletes memory if instructed |
| Patient ID tag | 1) not needed |

At least one synchronizing station embodiment does not require passive RFID tags and associated RFID readers, because all event and ID information is communicated by components utilizing radio frequency beacons, radio frequency receivers, and/or radio frequency transceivers (other than RFID readers). Also, since the zones may be relatively small (e.g., two to six feet) and RFID readers are not used in this embodiment, the required transmitting power is very low. As such, health care worker ID tags can be made very small and can operate a long time without battery replacement. Target zone and hand wash zone equipment (radio frequency beacons, receivers, transceivers, sensor suites) can also be battery-powered and avoid the need for hard-wiring. Thus, an entire embodiment can be installed into a hospital without any infrastructure or electrical wiring, with the possible exception of a hard wire connection for power to a few synchronizing stations and the central computer. (This assumes the synchronizing stations transmit information wirelessly, otherwise a few LAN connections will be required for the synchronizing stations.)

Figure 10A:
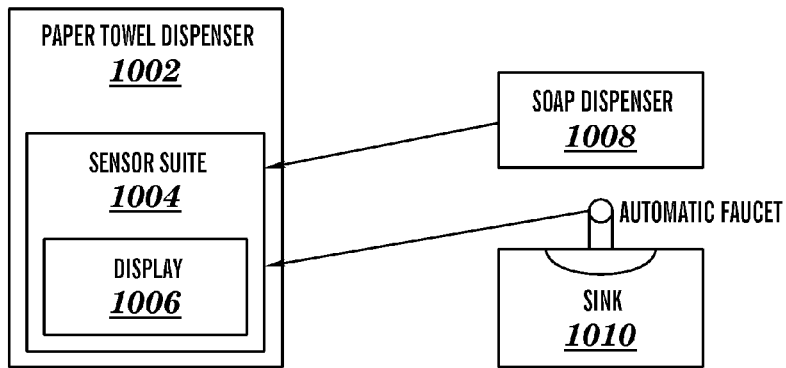
FIGS. 10A, 10B, and 10C, depicts a washroom station that includes a sensor suite, dispensers and at least one display in accordance with an embodiment.
Figure 10B:
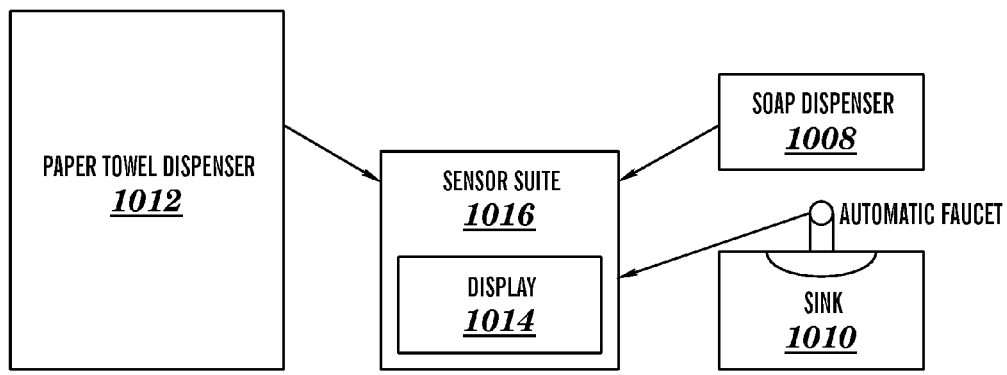
Figure 10C:
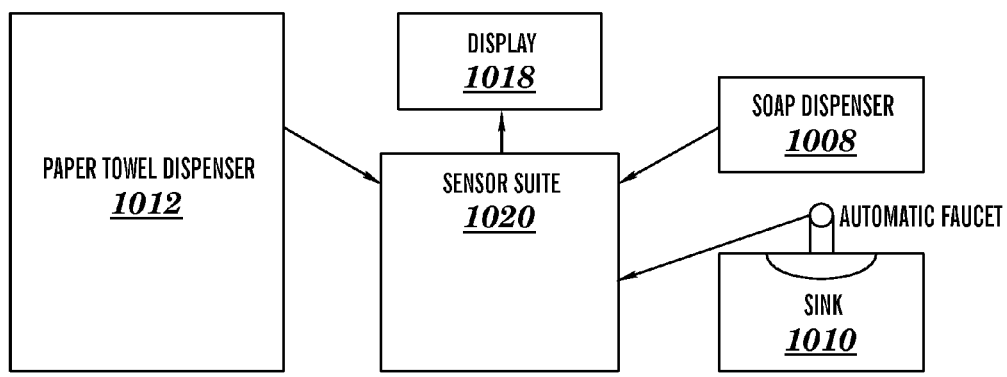

Turning now to FIG. 10, which includes FIG. 10A-10C. FIG. 10A depicts a hand wash station that includes a display 1006 in accordance with an embodiment, where the display 1006 is integrated with a sensor suite 1004 and a paper towel dispenser 1002, the sensor suite 1004 receiving inputs from multiple sources (a soap dispenser 1008 and an automatic faucet on a sink 1010). FIG. 10B depicts a hand wash station that includes one display 1014 in accordance with an embodiment, where the display 1014 is integrated with a stand-alone sensor suite 1016, the sensor suite 1016 receiving inputs from multiple sources (a soap dispenser 1008 and an automatic faucet on a sink 1010 and a paper towel dispenser 1012). FIG. 10C depicts a hand wash station that includes one display 1018 in accordance with an embodiment, wherein the display 1018 is a stand-alone unit receiving input from a sensor suite 1020. The sensor suite 1020 receives inputs from multiple sources (a soap dispenser 1008, an automatic faucet on a sink 1010 and a paper towel dispenser 1012).

In an embodiment, the displays are LCDs, however any display can be used. Particular design considerations that may be taken into account when selecting a display include battery operation, low or variable ambient lighting, requirement to display images as well as text (possibly including moving images; e.g. to illustrate accepted hand washing technique), ability to operate in humid environments, ability to cope with electrostatic build up, immunity to chemical contact of soap, and other factors. Examples of other types of displays include, but are not limited to, e-paper, mechanical displays (alpha-numeric only), electrophoresis, electrochromism, and field omission displays. Changing constraints may make other display technologies such LED and cathode ray tube, viable in other embodiments.

The specific embodiments described here pertain to a hand hygiene compliance system where a health care worker ID is presented or displayed on a dispenser, a hand wash station, or on some other object in order to indicate that a specific healthcare worker was verified as having complied with a hygiene protocol (e.g. washed their hands) (also referred to herein "received credit for" "washing hands"). However, different embodiments may include additional information in one or more displays. Additional information may include status of towel roll, soap, or any other dispensed material; status of battery or other device supplying energy to run the dispenser; a time log of hand wash station usage history to determine, for example, peak usage and/or best time to perform maintenance on the hand wash station; a log of any faults that may have occurred (e.g., stalled dispenser motor leading to shut down); and training on how to wash or dry hands effectively.

Embodiments of additional information shown on a display can range from routine hand wash confirmations to important messages concerning current events, healthcare alerts, etc. The displays may be able to provide information about nearby dispensers or hand wash stations in an embodiment with a network of dispensers or hand wash stations communicating amongst themselves or via a central computer. In an embodiment, it may be possible for a towel dispenser to annunciate the fact that a nearby soap dispenser is out of power and is unable to communicate that fact.

Some embodiments described herein do not penalize a health care worker for entering a waste station if he has not washed his hands since the previous target zone. This is based on the assumption that in typical use, a health care worker will be transporting contamination from a patient to the waste station, and it is impractical for the health care worker to wash his hands. However, in some embodiments, certain waste stations are not acceptable to approach from distant target zones. For example, if a health care worker departs a patient zone with waste on the east side of the building and there is a waste station on the east side, it may be unwise to allow the health care worker to deposit the waste in a waste station on the west side of the building. In an embodiment, the hand hygiene compliance system determines and reports non-compliance if the health care worker enters certain waste stations without washing their hands according to hand hygiene compliance policy.

As will be appreciated by one skilled in the art, aspects of the present invention may be embodied as a system, method, or computer program product. Accordingly, aspects of the present invention may take the form of an entirely hardware embodiment, an entirely software embodiment (including firmware, and resident software, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that may contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages as well as assembly language and/or machine code type languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, may be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer readable medium that may direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in other embodiment, the functions noted in the block occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts, or combinations of special purpose hardware and computer instructions.

While the invention has been described with reference to example embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method for performing sanitation compliance monitoring, the method comprising:
    receiving, at a computer, sanitation compliance data comprising a zone identifier corresponding to a first device in a zone and an entity identifier corresponding to a second device attached to a mobile entity in the zone, the zone defined by an area over which the first device and the second device communicate via one-way or two-way communication, wherein the zone is one of a target zone or a sanitation zone, the computer storing information associating each target zone with one or more approved sanitation zones, and wherein if the zone is a target zone, the zone does not overlap with a sanitation zone and if the zone is a sanitation zone, the zone does not overlap with a target zone;
    determining whether the mobile entity is compliant with a sanitation protocol associated with the zone, whereby compliance with the sanitation protocol associated with the zone is based at least in part on use of one of the one or more approved sanitation zones by the mobile entity and wherein use of a sanitation zone other than one of the one or more approved sanitation zones is not in compliance with the sanitation protocol; and
    updating a database with results of the determining.

2. The method of claim 1, further comprising changing the area of the zone by physically moving the first device.

3. The method of claim 1, wherein the area of the zone does not overlap the area of another zone.

4. The method of claim 1, wherein the zone is a target zone and the determining whether the zone is compliant with a sanitation protocol comprises determining a sanitation zone that is approved for the target zone.

5. The method of claim 4, wherein the target zone has one approved sanitation zone.

6. The method of claim 4, wherein the determining whether the mobile entity is compliant with a sanitation protocol further comprises verifying that the sanitation zone that is approved for the target zone is the most previous recorded activity of the mobile entity before the mobile entity entered the target zone.

7. The method of claim 4, wherein the determining whether the mobile entity is compliant with a sanitation protocol further comprises verifying that the sanitation zone that is approved for the target zone is a next recorded activity of the mobile entity after it exits the target zone.

8. The method of claim 1, wherein determining whether the mobile entity is compliant with a sanitation protocol comprises verifying that the mobile entity has satisfied a criteria of the sanitation protocol within a predetermined period of time.

9. The method of claim 1, wherein the target zone is a contamination zone.

10. The method of claim 1, wherein the mobile entity is a health care worker.

11. A method for performing sanitation compliance monitoring, the method comprising:
    receiving a notification at a circuit in a mobile entity identification (ID) tag that a zone ID tag has been detected, each zone ID tag corresponding to a zone and having a unique zone zone and each of the sanitation zones do not overlap, and each target zone is associated with (a) one or more approved sanitation zones and (b) a sanitation protocol, whereby compliance with the sanitation protocol associated with the zone is based at least in part on use of one of the one or more approved sanitation zones by the health care worker, and wherein use of a sanitation zone other than one of the one or more approved sanitation zones is not in compliance with the sanitation protocol.

12. The method of claim 11, further comprising deleting contents of the database in response to the transmitting.

13. The method of claim 11, wherein the mobile entity tag is a radio frequency transceiver and the zone tag is a radio frequency transmitter or transceiver.

14. The method of claim 11, wherein the mobile entity ID tag includes a radio frequency identifier (RFID) reader and the zone ID tag is a RFID tag.

15. A system for performing sanitation compliance monitoring, the system comprising:

a first device in communication with a database;
one or more second devices in communication with the database;
a target zone defined by a first area over which a mobile device worn by a health care worker and the first device communicate; and
one or more sanitation zones each defined by a second area over which the mobile device worn by the health care worker and one of the second devices communicate, wherein the target identifier, wherein each zone is one of a target zone or a sanitation zone, each target zone being associated with one or more approved sanitation zones and each target zone being associated with a compliance protocol, whereby compliance with the compliance protocol associated with each target zone is based at least in part on use of one of the one or more approved sanitation zones by a mobile entity associated with the mobile entity ID tag, wherein use of a sanitation zone other than one of the one or more approved sanitation zones is not in compliance with the sanitation protocol, and wherein if the zone is a target zone, the zone does not overlap with a sanitation zone and if the zone is a sanitation zone, the zone does not overlap with a target zone;
storing, in a database on the mobile entity ID tag, the unique zone identifier corresponding to the zone ID tag, the storing in response to the receiving; and
periodically transmitting contents of the database to a central computer.

16. The system of claim 15, wherein the first device transmits data to the database responsive to a communication between the first device and the mobile device worn by the health care worker, and the second device transmits data to the database responsive to a communication between the second device and the mobile device worn by the health care worker.

17. The system of claim 16, wherein the data transmitted by the first device includes a unique identifier associated with the first device, a unique identifier associated with the mobile device, and a time stamp.

18. The system of claim 15, wherein the target zone is a contamination zone.

19. The system of claim 15, wherein the target zone is an aseptic zone.

20. The system of claim 15, wherein a sensor suite is located in the sanitation zone and the sensor suite is in communication with the second device.

* * * * *

UNITED STATES PATENT AND TRADEMARK OFFICE
CERTIFICATE OF CORRECTION

PATENT NO. : 9,672,726 B2
APPLICATION NO. : 13/291679
DATED : June 6, 2017
INVENTOR(S) : Borke et al.

It is certified that error appears in the above-identified patent and that said Letters Patent is hereby corrected as shown below:

Column 24
Claim 11 should read:
--11. A method for performing sanitation compliance monitoring, the method comprising:
  receiving a notification at a circuit in a mobile entity identification (ID) tag that a zone ID tag has been detected, each zone ID tag corresponding to a zone and having a unique zone identifier, wherein each zone is one of a target zone or a sanitation zone, each target zone being associated with one or more approved sanitation zones and each target zone being associated with a compliance protocol, whereby compliance with the compliance protocol associated with each target zone is based at least in part on use of one of the one or more approved sanitation zones by a mobile entity associated with the mobile entity ID tag, wherein use of a sanitation zone other than one of the one or more approved sanitation zones is not in compliance with the sanitation protocol, and wherein if the zone is a target zone, the zone does not overlap with a sanitation zone and if the zone is a sanitation zone, the zone does not overlap with a target zone;
  storing, in a database on the mobile entity ID tag, the unique zone identifier corresponding to the zone ID tag, the storing in response to the receiving; and
  periodically transmitting contents of the database to a central computer.--

Column 25
Claim 15 should read:
--15. A system for performing sanitation compliance monitoring, the system comprising:
  a first device in communication with a database;
  one or more second devices in communication with the database;
  a target zone defined by a first area over which a mobile device worn by a health care worker and the first device communicate; and
  one or more sanitation zones each defined by a second area over which the mobile device worn by the health care worker and one of the second devices communicate, wherein the target zone and each of the sanitation zones do not overlap, and each target Signed and Sealed this
Fifth Day of September, 2017

Joseph Matal
*Performing the Functions and Duties of the*
*Under Secretary of Commerce for Intellectual Property and*
*Director of the United States Patent and Trademark Office* zone is associated with (a) one or more approved sanitation zones and (b) a sanitation protocol, whereby compliance with the sanitation protocol associated with the zone is based at least in part on use of one of the one or more approved sanitation zones by the health care worker, and wherein use of a sanitation zone other than one of the one or more approved sanitation zones is not in compliance with the sanitation protocol.--